US011559604B2

(12) United States Patent
Roy et al.

(10) Patent No.: US 11,559,604 B2
(45) Date of Patent: Jan. 24, 2023

(54) NERVE CONDUITS

(71) Applicant: University of Westminster, London (GB)

(72) Inventors: Ipsita Roy, Southampton (GB); Rinat Nigmatullin, Bristol (GB); Pooja Basnett, Pinner (GB); Barbara Lukasiewicz, Compton (GB)

(73) Assignee: University of Westminster, London (GB)

( * ) Notice: Subject to any disclaimer, the term of this patent is extended or adjusted under 35 U.S.C. 154(b) by 478 days.

(21) Appl. No.: 16/642,793

(22) PCT Filed: Aug. 30, 2018

(86) PCT No.: PCT/GB2018/052442
§ 371 (c)(1),
(2) Date: Feb. 27, 2020

(87) PCT Pub. No.: WO2019/043383
PCT Pub. Date: Mar. 7, 2019

(65) Prior Publication Data
US 2020/0261617 A1 Aug. 20, 2020

(30) Foreign Application Priority Data

Aug. 31, 2017 (GB) ..................................... 1713985
Sep. 14, 2017 (GB) ..................................... 1714816

(51) Int. Cl.
*A61L 27/26* (2006.01)
*A61L 27/58* (2006.01)
*C08L 67/04* (2006.01)

(52) U.S. Cl.
CPC .............. *A61L 27/26* (2013.01); *A61L 27/58* (2013.01); *C08L 67/04* (2013.01); *A61L 2430/32* (2013.01)

(58) Field of Classification Search
None
See application file for complete search history.

(56) References Cited

U.S. PATENT DOCUMENTS

| | | | |
|---|---|---|---|
| 7,504,556 | B2 | 3/2009 | Madison et al. |
| 8,039,237 | B2 | 10/2011 | Martin et al. |
| 8,956,835 | B2 | 2/2015 | Nakas et al. |
| 2001/0031974 | A1 | 10/2001 | Hadlock et al. |
| 2004/0220355 | A1 | 11/2004 | Whitehouse |
| 2011/0166318 | A1 | 7/2011 | Jiang et al. |
| 2011/0236974 | A1 | 9/2011 | Ogle et al. |
| 2013/0122559 | A1 | 5/2013 | Lan et al. |
| 2014/0039603 | A1 | 2/2014 | Wang |
| 2015/0305899 | A1 | 10/2015 | Harrington et al. |

FOREIGN PATENT DOCUMENTS

| | | |
|---|---|---|
| AU | 2004257701 B2 | 9/2007 |
| CN | 101555505 A | 10/2009 |
| CN | 101760485 A | 6/2010 |
| EP | 2546352 A1 | 1/2013 |
| JP | 2005041980 A | 2/2005 |
| WO | 0056376 A1 | 9/2000 |
| WO | 2011146484 A2 | 11/2011 |
| WO | 2012064526 A1 | 5/2012 |
| WO | 2013184822 A1 | 12/2013 |
| WO | 2016166292 A1 | 10/2016 |
| WO | 2019043383 A1 | 3/2019 |

OTHER PUBLICATIONS

Akaraonye E et al. "Poly(3-hydroxybutyrate) production by Bacillus cereus SPV using sugarcane molasses as the main carbon source," Biotechnol. J. (2012), 7, 293-303.
Amache et al. "Advances in PHAs Production," Chemical Engineering Transactions (2013) 32: 931-936.
Basnett et al. "Novel Poly(3-hydroxyoctanoate)/Poly(3-hydroxybutyrate) blends for medical applications," Reactive and Functional Polymers. 73 (10); 1340-1348, 2013.
Basnett, P, "Biosynthesis of polyhydroxyalkanoates, their novel blends and composites for biomedical applications", (2014) Abstract of PhD thesis, 4 pages.
Dubey P, "Development of cardiac patches using medium chain length polyhydroxyalkanoates for cardiac tissue engineering", (2017) Abstract of PhD thesis, 3 pages.
Hart et al. "Exogenous Leukaemia Inhibitory Factor Enhances Nerve Regeneration After Late Secondary Repair Using a Bioartificial Nerve Conduit," (2003) Br. J. Plast. Surg. 56: 444-450.
Hazari et al. "A resorbable nerve conduit as an alternative to nerve autograft in nerve gap repair," (1999) Br. J. Plast. Surg. 52(8): 653-657.
Hong et al. "Effect of C:N molar ratio on monomer composition of polyhydroxyalkanoates produced by Pseudomonas mendocina 0806 and Pseudomonas pseudoalkaligenus YS1," Appl Biochem Biotechnol. 84-86:971-80 (2000).
International Search Report and Written Opinion issued in International Application No. PCT/GB2018/052443, dated Jan. 30, 2019, 16 pages.

(Continued)

*Primary Examiner* — Robert A Wax
*Assistant Examiner* — Randeep Singh
(74) *Attorney, Agent, or Firm* — Dorsey & Whitney LLP

(57) ABSTRACT

The invention provides bioresorbable nerve guidance conduits made from polymer blends which include polyhydroxyalkanoates (PHAs). In particular, the invention provides nerve guidance conduits having a body which comprises a polymer blend comprising: (a) from 60 to 98 wt. % of a first component which is a PHA copolymer comprising two or more different medium chain length hydroxyalkanoate monomer units; and (b) from 2 to 40 wt. % of a second component which is either a PHA homopolymer containing a short chain length hydroxyalkanoate monomer unit, or a polylactide (PLA). The invention further relates to polymer blends comprising (a) and (b).

29 Claims, 8 Drawing Sheets

(56) References Cited

OTHER PUBLICATIONS

Kaufmann et al. "CRT-700 Endovascular AAA Bioabsorbable Graft—A Pilot Study Demonstrating A Confluent Endothelium And Neotissue Formation In Swine," JACC: Cardiovascular Interventions. 8 (2), Suppl S, 2015, S43.
Le Muer et al. "Production of medium-chain-length polyhydroxyalkanoates by sequential feeding of xylose and octanoic acid in engineered Pseudomonas putida KT2440," BMC Biotechnology (2012) 12: 53.
Lizarraga-Valderrama et al. "Nerve tissue engineering using blends of polyl(hydroxyalkanoates) for peripheral nerve regeneration," Engineering in Life Sciences, 2015, 15, 612-621.
Mohanna et al. "Composite PHB-GGF conduit for long nerve gap repair: A long-term evaluation," (2005) Scand. J. Plast. Reconstr. Surg. Hand Surg. 39(3): 129-137.
Mosahebi et al. "Addition of Fibronectin to Alginate Matrix Improves Peripheral Nerve Regeneration in Tissue-Engineered Conduits," (2003) Tissue Eng. 9: 209-218.
Mosahebi et al. "Effect of Allogeneic Schwann Cell Transplantation on Peripheral Nerve Regeneration," (2002) Exp. Neurol. 173: 213-223.
Mosahebi et al. "Retroviral labeling of Schwann cells: In vitro characterization and in vivo transplantation to improve peripheral nerve regeneration," (2001) Glia. 34: 8-17.
Panchai B, "Production of Polyhydroxyalkanoates by Pseudomonas mendocina using vegetable oils and their characterisation", (2017) Abstract of PhD thesis, 3 pages.
Philip S et al. "Effect of impeller speed and pH on the production of Poly(3-hydroxybutyrate) using Bacillus cereus SPV," Biomacromolecules (2009), 10, 691-699 691.
Rai et al. "Poly-3-hydroxyoctanoate P(3HO), a Medium Chain Length Polyhydroxyalkanoate Homopolymer from Pseudomonas mendocina," Biomacromolecules (2011), 12, 2126-2136.
Scholl et al. "Characterization of a new Pseudomonas isolate, capable of accumulating polyesters of medium chain length 3-hydroxyalkanoic acids," Journal of Biotechnology, 1996, 47, 53-63.
Search Report dated Feb. 28, 2018 for British patent application No. 1713994.0, 5 pages.
Shrivastav et al. "Advances in the Applications of Polyhydroxyalkanoate Nanoparticles for Novel Drug Delivery System," (2013) Nanobiotechnology. Article ID 581684, 12 pages.
Sukan et al. "Agro-Industrial Waste Materials as Substrates for the Production of Poly(3-Hydroxybutyric Acid)," Journal of Biomaterials and Nanobiotechnology, (2014) 5, 229-240.
Tian et al. "Production of polyesters consisting of medium chain length 3-hydroxyalkanoic acids by Pseudomonas mendocina 0806 from various carbon sources," (2000) Antonie Leeuwenhoek 77:31-36.
Valappil et al. "Large-scale production and efficient recovery of PHB with desirable material properties, from the newly characterised Bacillus cereus SPV," Journal of Biotechnology 132 (2007) 251-258.
Valappil et al. "Polyhydroxyalkanoate (PHA) biosynthesis from structurally unrelated carbon sources by a newly characterized *Bacillus* spp," Journal of Biotechnology 127 (2007) 475-487.
Valappil et al. "Polyhydroxyalkanoate biosynthesis in Bacillus cereus SPV under varied limiting conditions and an insight into the biosynthetic genes involved," Journal of Applied Microbiology 104 (2008) 1624-1635.
Vroman et al. "Biodegradable Polymers" (2009) Materials. 2(2): 307-344.
Wang et al. "Optimization of medium composition for 3-hydroxycarboxylic acid production by Pseudomonas mendocina-biodegraded polyhydroxybutyrate," Biotechnol Appl Biochem (2015) 62(2):260-7.
Wang et al. "Thermal and Thermomechanical Behaviour of Polycaprolactone and Starch/Polycaprolactone Blends for Biomedical Applications," (2005) Macromol. Mater. Eng. 290 (8): 792-801.
Young et al. "Poly-3-hydroxybutyrate (PHB): A Resorbable Conduit for Long-Gap Repair in Peripheral Nerves," (2002) Br. J. Plast. Surg. 55: 235-240.
Mao et al. "Purification and characterization of two extracellular polyhydroxyalkanoate depolymerases from Pseudomonas mendocina," Biotechnol Lett: 35(11):1919-24, Jul. 24, 2013.
Bian Y Z et al. "Evaluation of poly(3-hydroxybutyrate-co-3-hydroxyhexanoate) conduits for peripheral nerve regeneration," Biomaterials, Oct. 11, 2008, 30 (2), 217-225.
Can et al. "Investigation of PLLA/PCL Blends and Paclitaxel Release Profiles," Oct. 25, 2011, AAPS PharmSciTech. 12 (4): 1442-1453.
Shabna et al. "Indigenously produced polyhydroxyalkanoate based copolymer as cellular supportive biomaterial," Journal of Biomedical Materials Research Part A, Nov. 12, 2013, 102, 3470-3476.
Guo et al. "Comparison of medium-chain-length polyhydroxyalkanoates synthases from Pseudomonas mendocina NK-01 with the same substrate specificity" Microbiol Res. Dec. 11, 2012, 168(4):231-7.
Hein et al. "Cloning, characterization and comparison of the Pseudomonas mendocina polyhydroxyalkanoate synthases Phac1 and PhaC2," Appl Microbiol Biotechnol. 58(2):229-36, Dec. 12, 2001.
Nerkar et al. "Melt compounded blends of short and medium chain-length Poly-3-hydroxyalkanoates," J Polym. Environ, Dec. 19, 2013, 22, 236-243.
Search Report dated Feb. 27, 2018 for British patent application No. 1713985.8, 4 pages.
Sukan et al. "Dual production of biopolymers from bacteria," Carbohydrate polymers, Mar. 7, 2015, 126; 47-51.
Akaraonye E et al., "Production of polyhydroxyalkanoates: the future green materials of choice," J Chem Technol Biotechnol; 85:732-743, Apr. 23, 2010.
Ashby et al. "Synthesis of Short-/Medium-Chain-Length Poly(hydroxyalkanoate) Blends by Mixed Culture Fermentation of Glycerol," Biomacromolecules, Apr. 28, 2005, 6, 2106-2112.
Nair et al. "Biodegradable polymers as biomaterials" May 24, 2007, Prog. Polym. Sci. 32(8-9): 762-798.
Guo et al. "Simultaneous production and characterization of medium-chain-length polyhydroxyalkanoates and alginate oligosaccharides by Pseudomonas mendocina NK-01," Appl Microbiol Biotechnol: 92(4):791-801, May 27, 2011.
Kroumova et al. "Biochemical observations on medium-chain-length polyhydroxyalkanoate biosynthesis and accumulation in Pseudomonas mendocina," Arch Biochem Biophys. 405(1):95-103, Jun. 26, 2002.
Singh et al. "Bacillus subtilis as potential producer for Polyhydroxyalkanoates," Jul. 20, 2009, Microbial Cell Factories. 8:38.
Haywood et al. "Accumulation of a Polyhydroxyalkanoate Containing Primarily 3-Hydroxydecanoate from Simple Carbohydrate Substrates by *Pseudomonas* sp. Strain NCIMB 40135," Applied and Environmental Microbiology, Aug. 15, 1990, 56(11), 3354-3359.
International Search Report and Written Opinion issued in International Application No. PCT/GB2018/052442, dated Oct. 19, 2018, 10 pages.

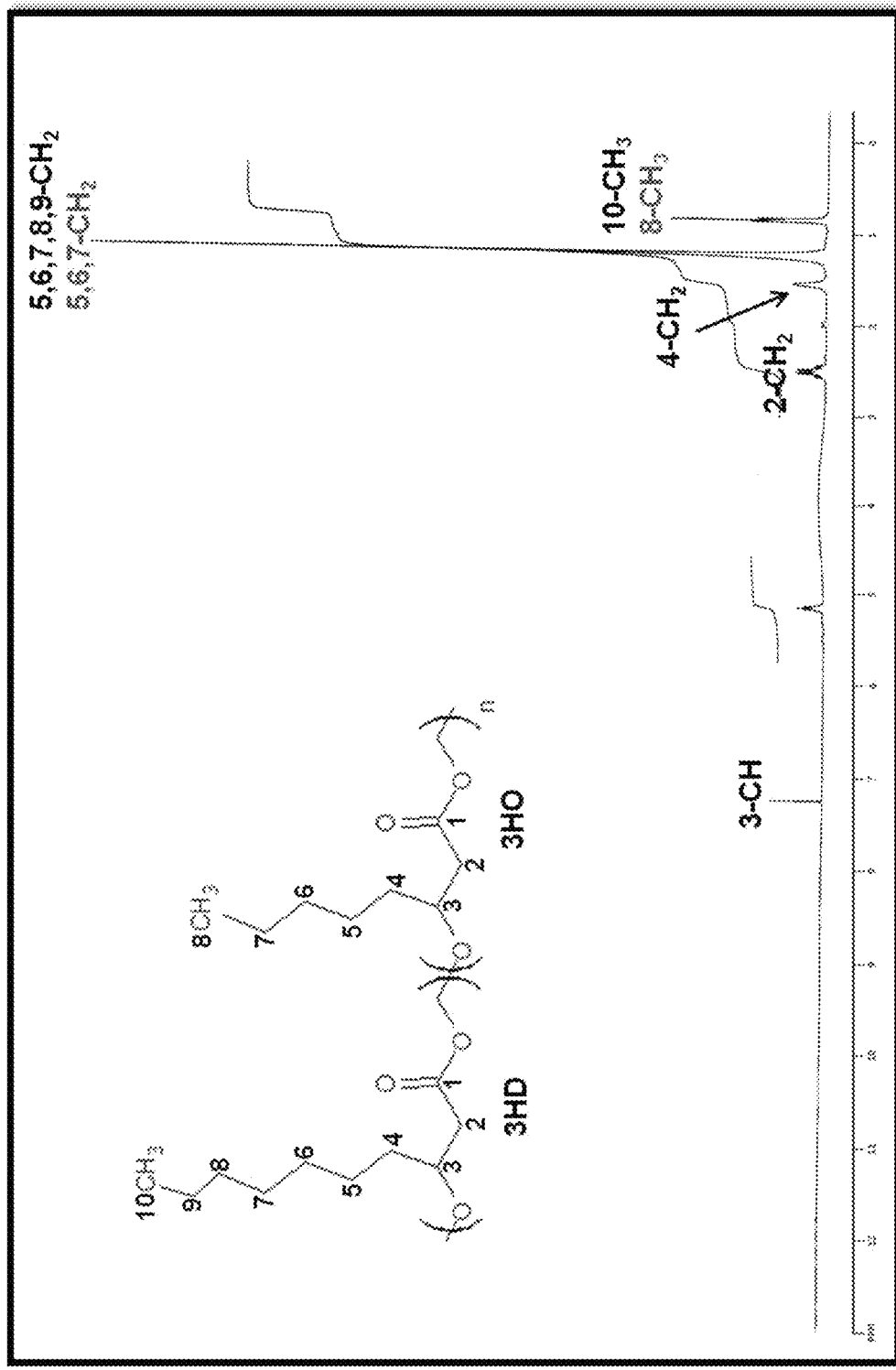
Fig. 1 (continued on next page)

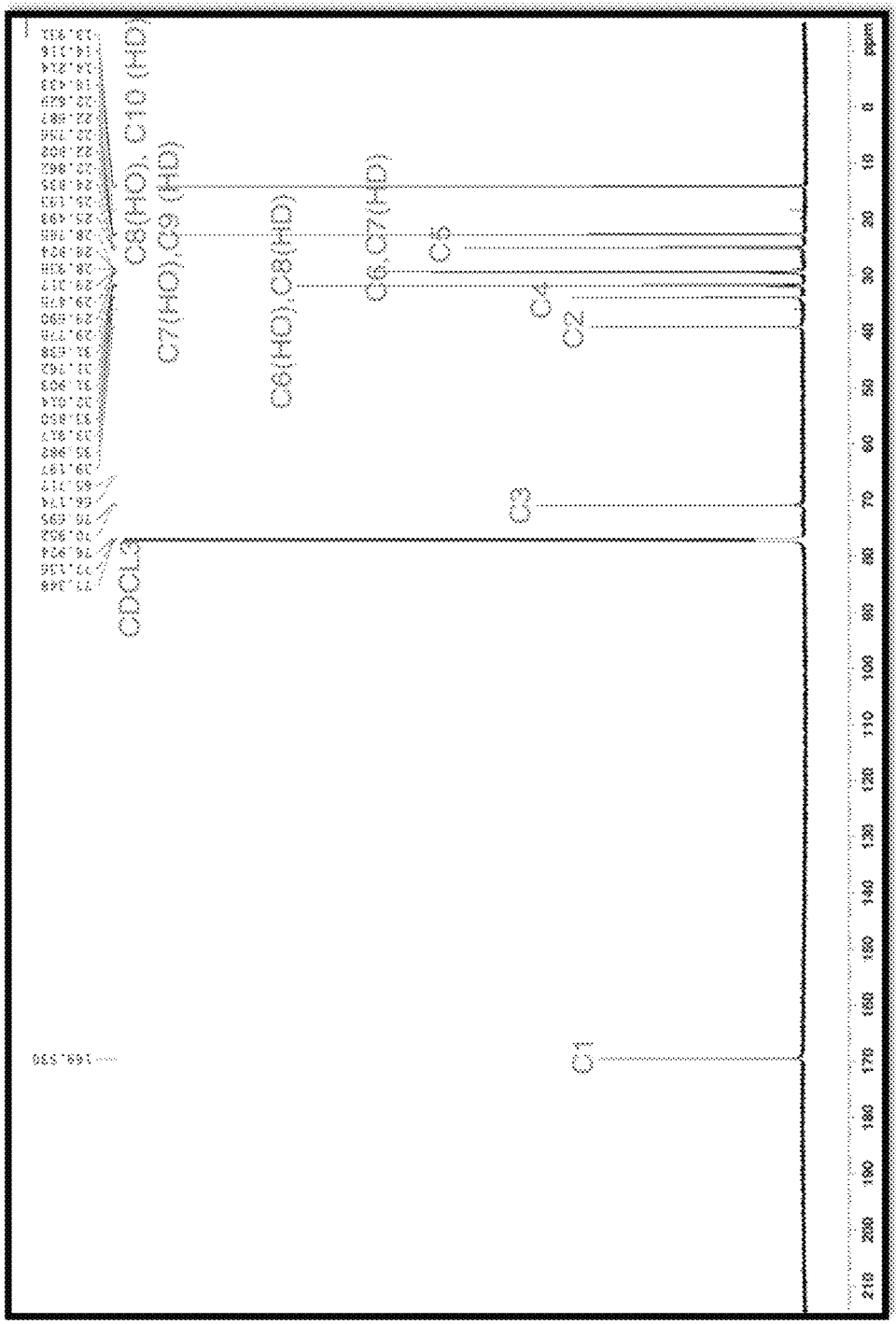
Figure 1 - NMR spectra of P(3HO-3HD) produced by *Pseudomonas mendocina* CH50 using glucose
Fig. 1 (continued from previous page)

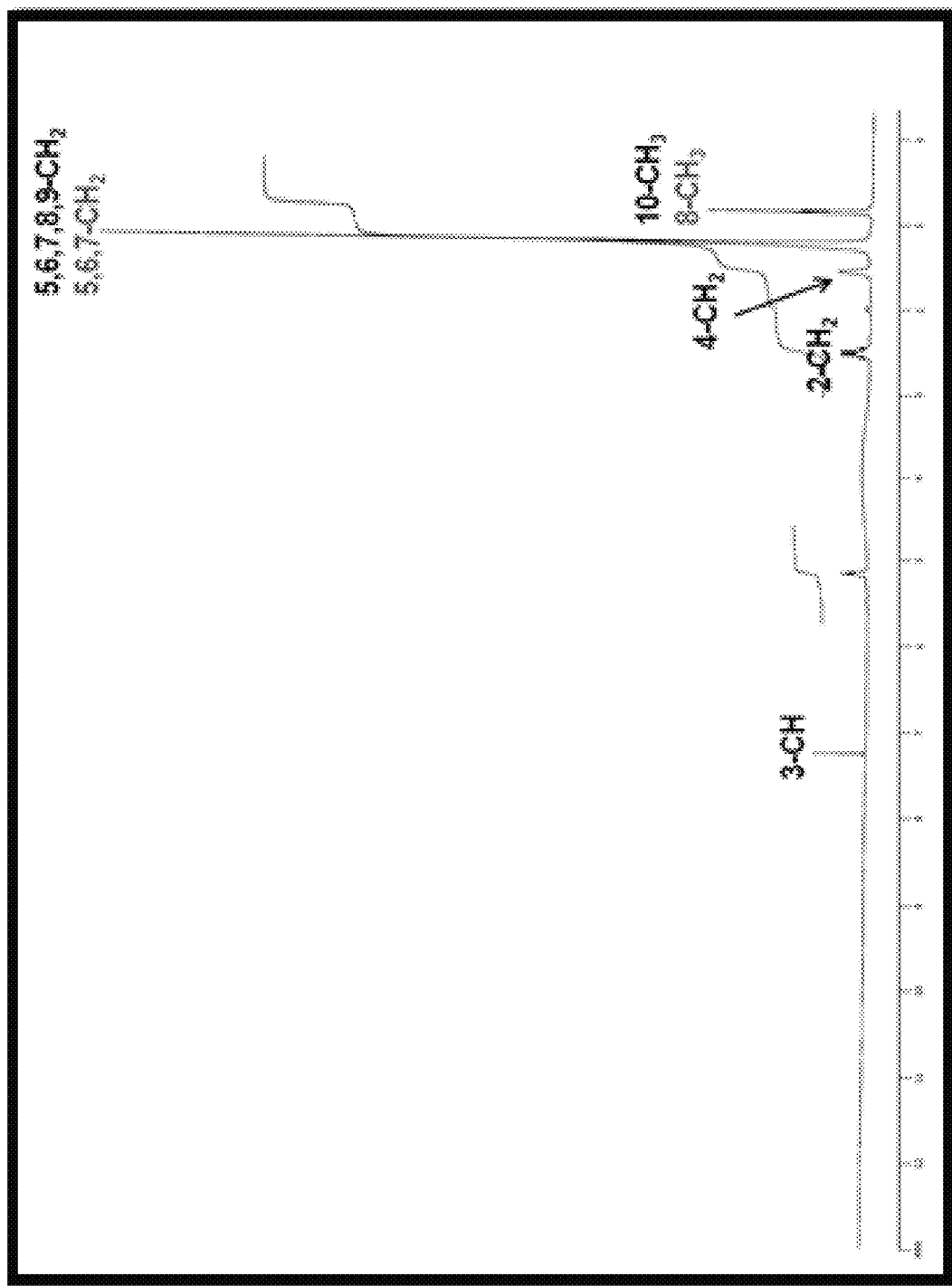
Fig. 2 (continued on next page)

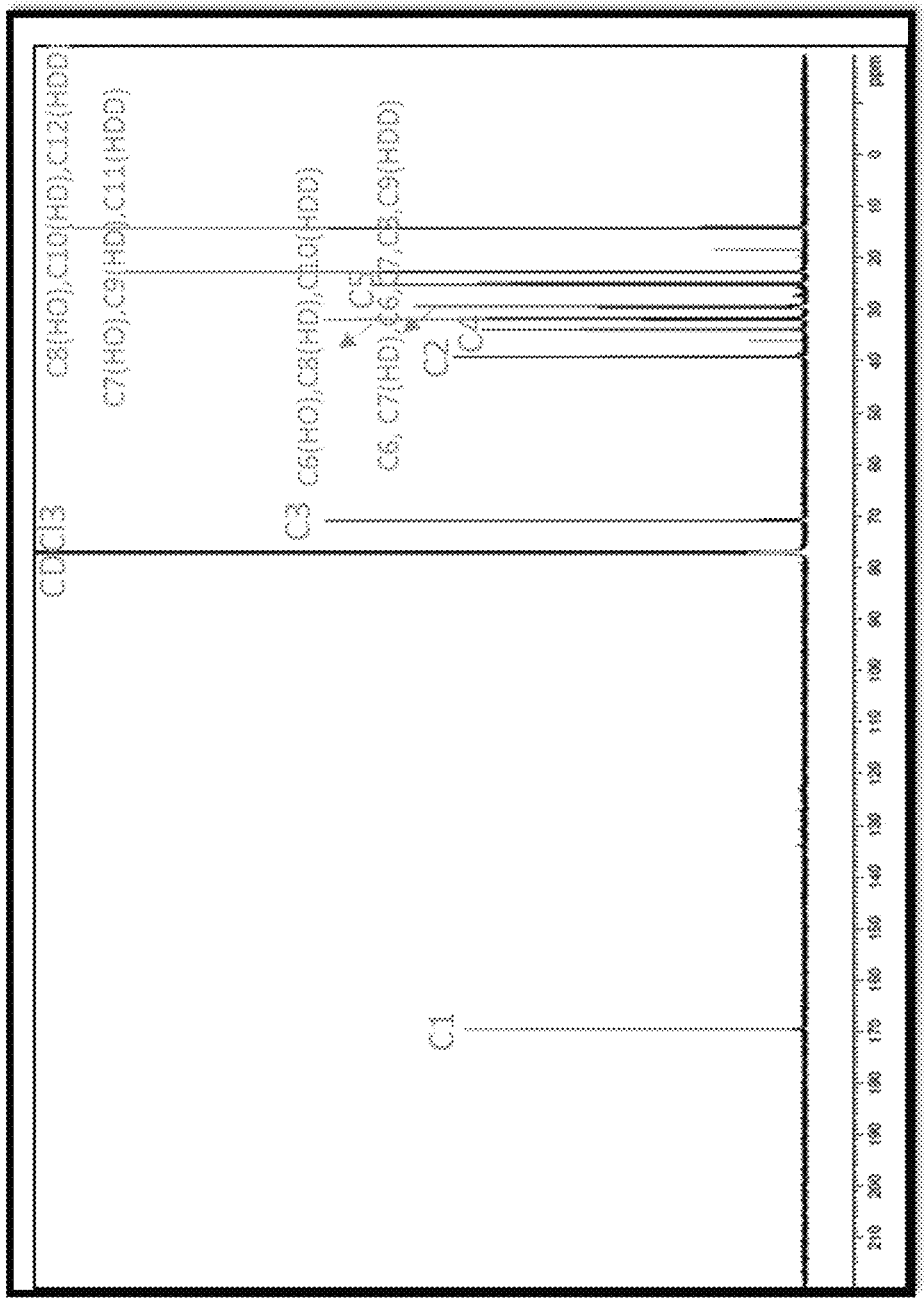
Figure 2 - NMR spectra of P(3HO-3HD-3HDD) produced by *Pseudomonas mendocina* CH50 using coconut oil
Fig. 2 (continued from previous page)

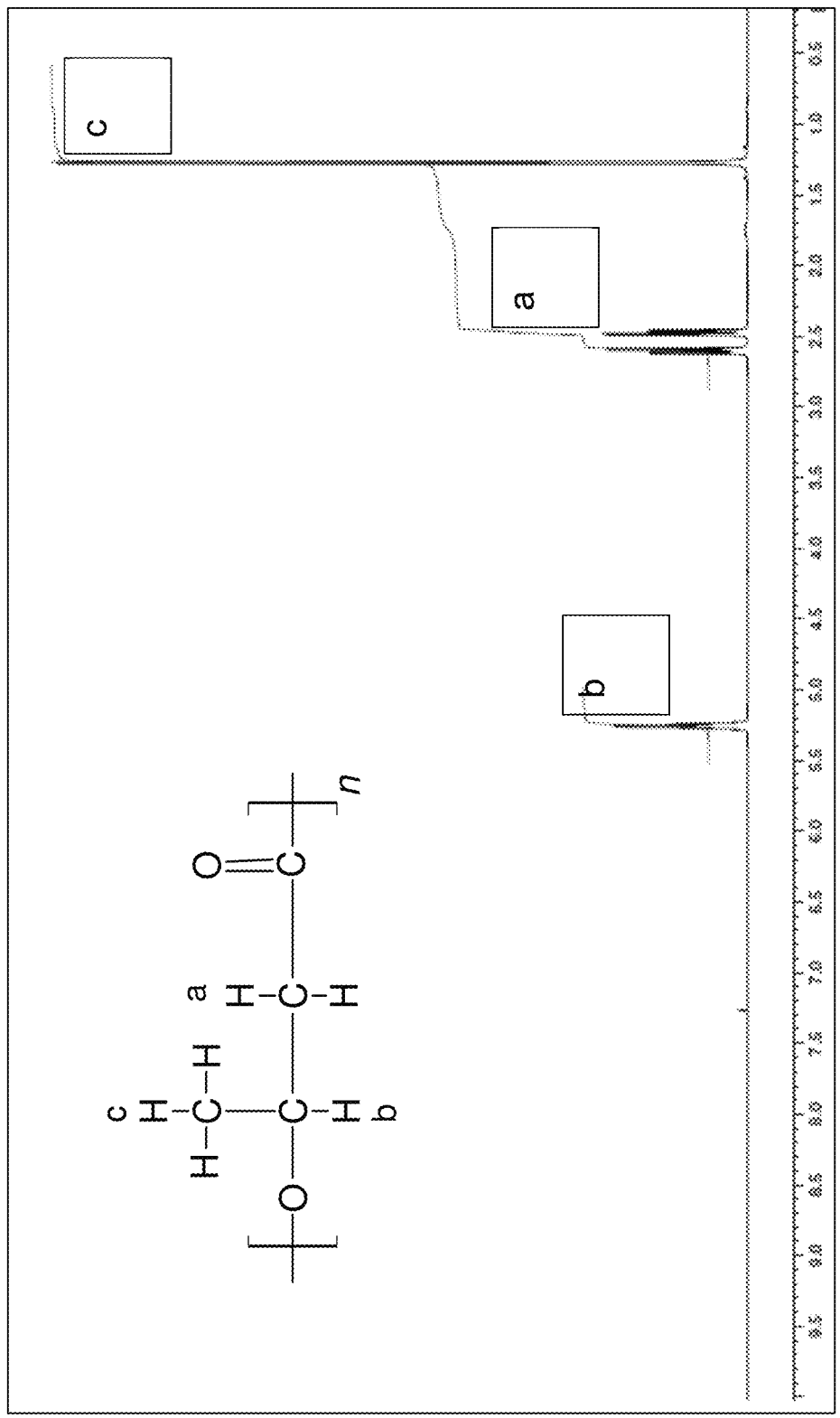
Fig. 3 (continued on next page)

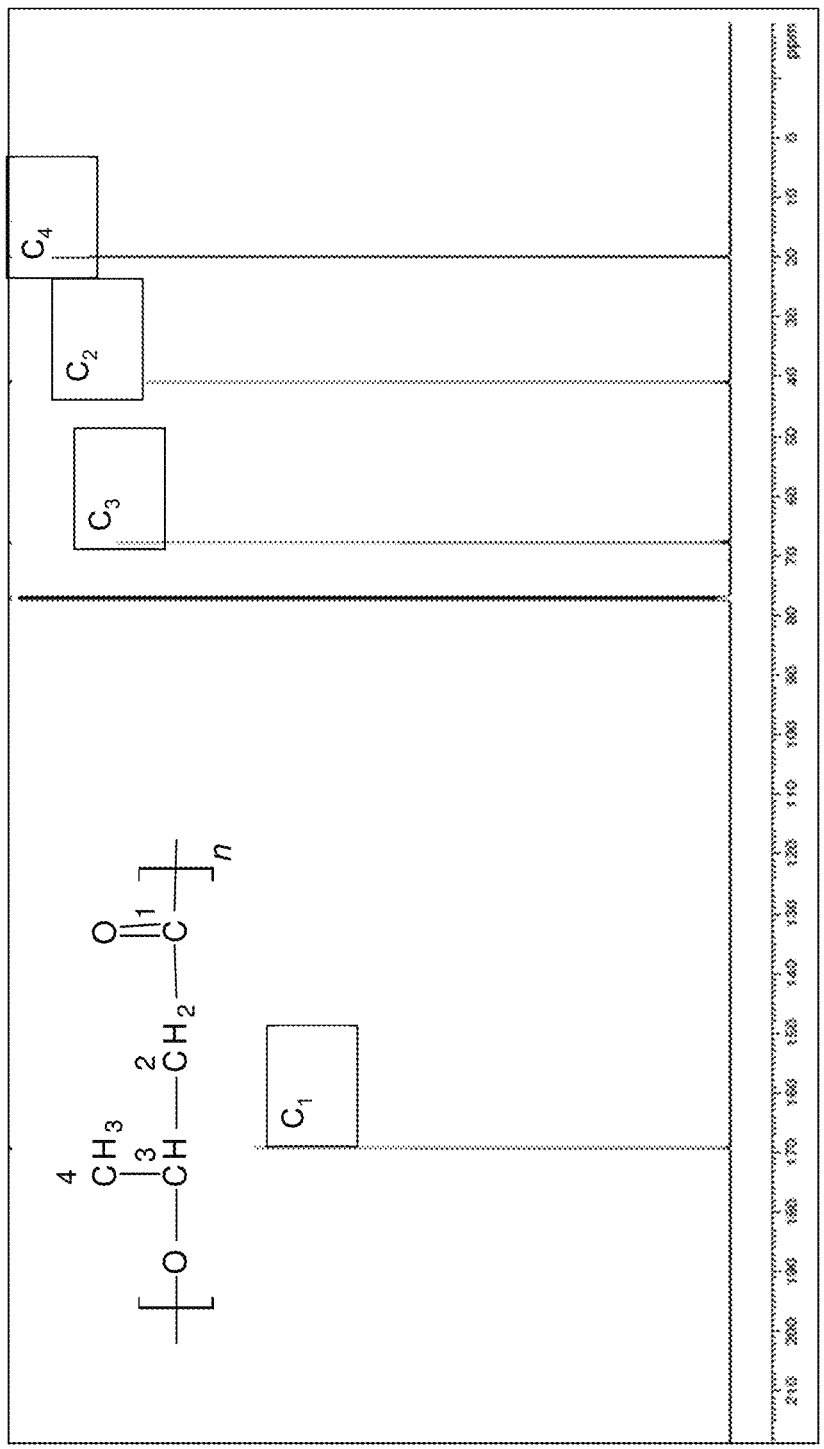
Figure 3 - NMR spectra of P(3HB) produced by *Bacillus subtilis* OK2 using glucose

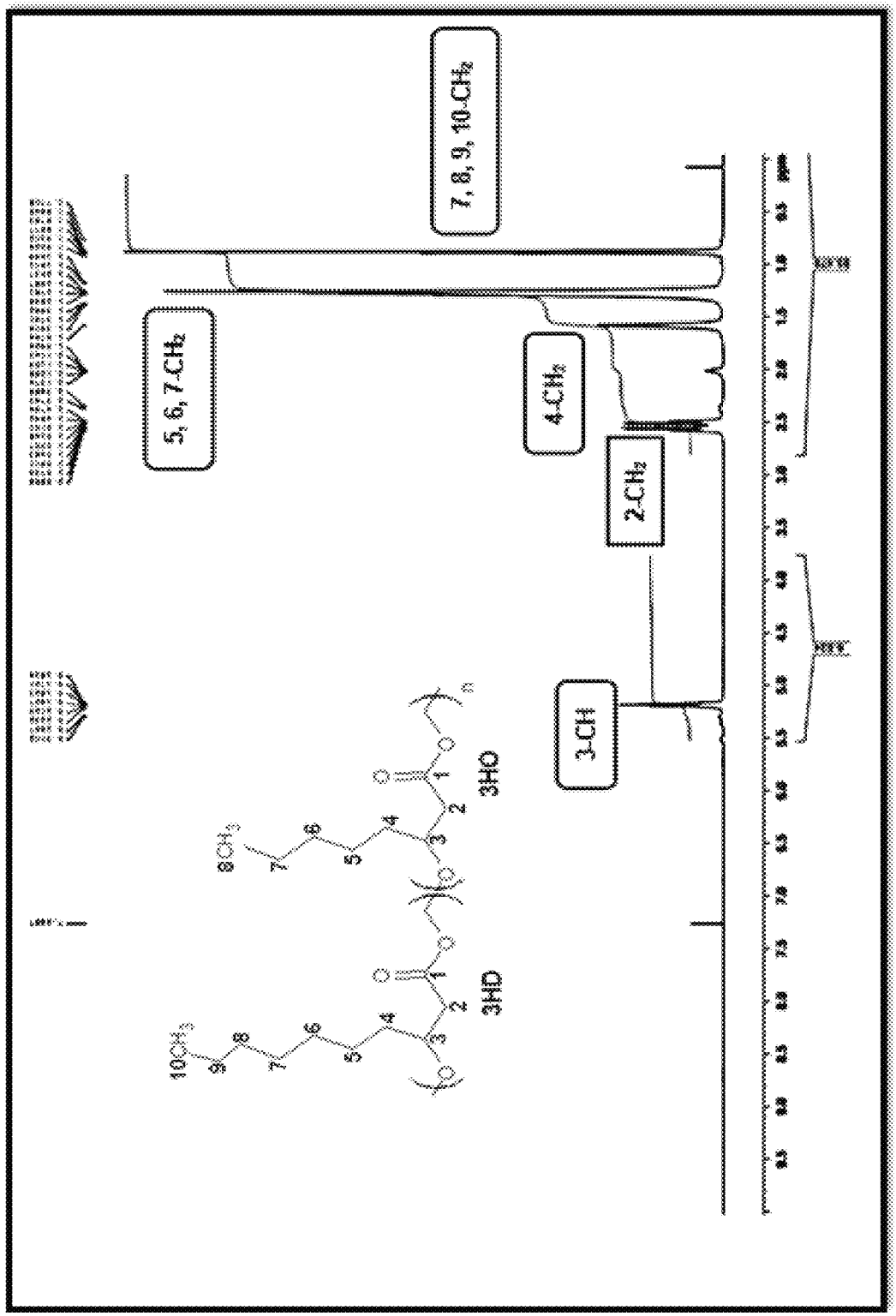
Fig. 4 (continued on next page)

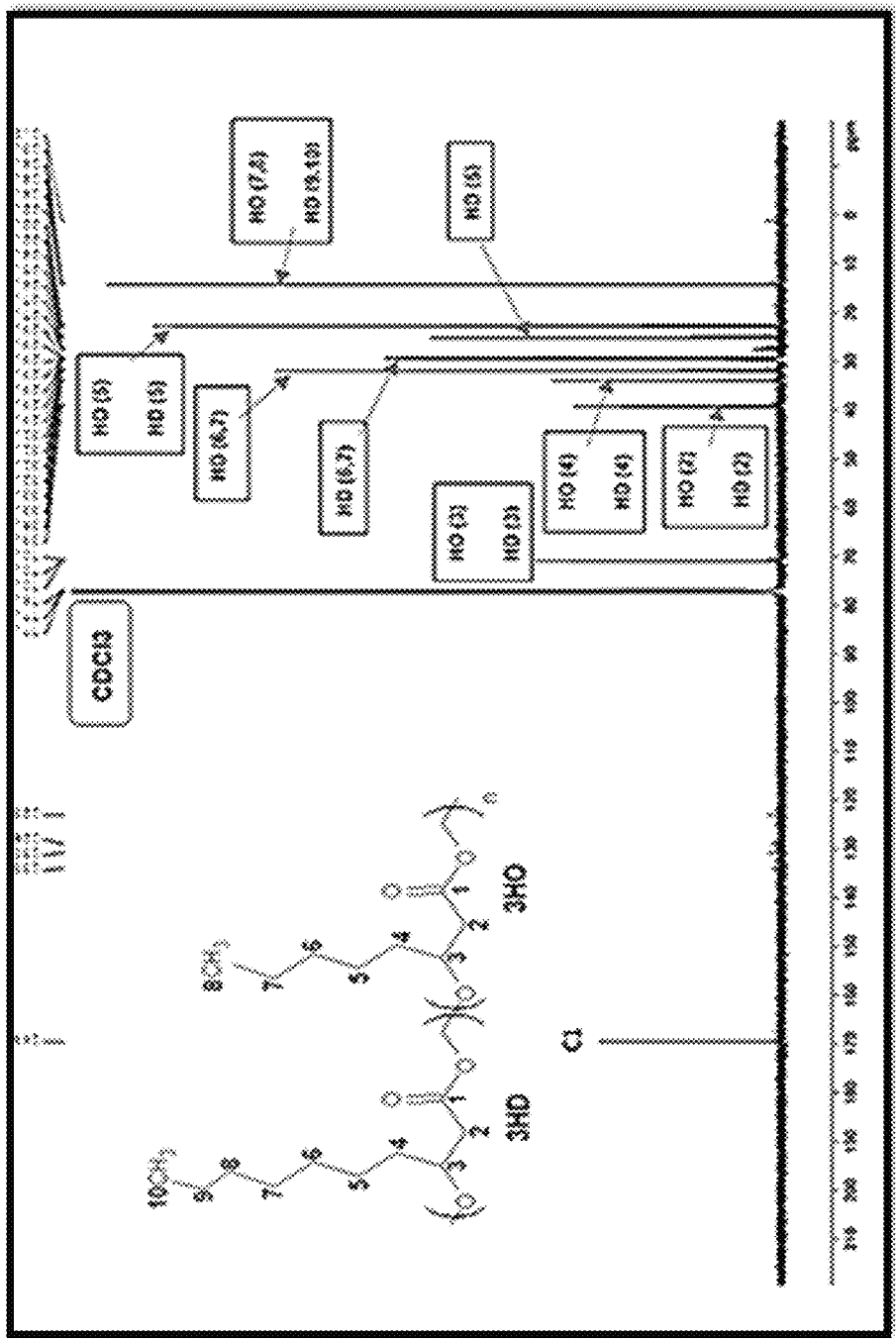
Figure 4 - NMR spectra of P(3HO-3HD) produced by *Pseudomonas mendocina* CH50 using sugarcane molasses

NERVE CONDUITS

FIELD OF THE INVENTION

The present invention generally relates to nerve repair materials, and more particularly to bioresorbable nerve guidance conduits (also generally known as artificial nerve conduits or artificial nerve grafts). These are made from polymer blends which include polyhydroxyalkanoates (PHAs) (herein referred to as "PHA blends"). The invention further relates to novel PHA blends and to methods for their preparation.

The invention further relates to certain novel PHA materials produced by the microorganism *Pseudomonas mendocina* CH50, to methods for the production of such PHA materials, and their use in the preparation of a PHA blend which may be used as a nerve guidance conduit material.

BACKGROUND OF THE INVENTION

Peripheral nerve injuries affect about 2.8% of trauma patients. In many cases there is a significant loss of sensation and motor function which can have a considerable impact on the quality of life. In the case of complete nerve transection, the severed ends of the nerve often retract further increasing the loss of nerve function. Peripheral nerves have a remarkable capacity for regeneration and are able to repair themselves when the injuries present a gap of less than 5 mm to bridge. For injuries resulting in nerve damage with gaps of more than 5 mm, however, treatment is most commonly attempted using autologous nerve graft repair. When nerve damage is even more extreme and gaps exceed 3 cm, allografts, autografts, and vascularised nerve grafts may be used.

Peripheral nerve repair using nerve autografts has several limitations, including donor site morbidity, scar tissue invasion, scarcity of donor nerves, inadequate return of function and aberrant regeneration. Several clinically approved artificial nerve guidance conduits made from various biomaterials have overcome some of these limitations. However, nerve conduits made from synthetic materials can trigger immune responses, induce scar tissue and may also release compounds that are detrimental to the nerve regeneration process.

A number of materials including nano-structured materials and biochemical factors have been explored in an attempt to improve the quality of artificial nerve conduits, and currently there are several which are commercially available. These take the form of a simple hollow tube with a single lumen, are made from either synthetic or natural materials and are available in different designs and sizes. Materials that have been used include poly(D,L-lactide-ε-caprolactone) (PLCL), polyglycolic acid (PGA), polyvinyl alcohol (PVA), collagen type I (COLI) and extracellular matrix (ECM).

A range of materials have also been used experimentally to produce nerve guidance conduits, such as aliphatic polyesters, polylactic acids, polycaprolactones, polyurethanes, silicones, collagens, glycoproteins, polypeptides, polyhydroxyalkanoates (PHAs), polysaccharides, proteins and acellular or extracellular matrices.

Polyhydroxyalkanoates (PHAs) are hydrophobic storage polymers which are polyesters of 3-, 4-, 5- and 6-hydroxyalkanoic acids produced by a variety of bacterial species from renewable carbon sources under nutrient-limiting conditions. They are biodegradable and biocompatible in nature. PHAs are attractive materials for biomedical applications because of their natural origin, enhanced biocompatibility, biodegradability, lack of cytotoxicity and ability to support cell growth and cell adhesion. Therefore, there has been a great interest in the commercial use of these biodegradable polyesters for industrial as well as biomedical applications. Depending on the total carbon chain length in the monomeric units, PHAs can be classified as short chain length (SCL) or medium chain length (MCL) PHAs. SCL-PHAs are brittle and have a high melting temperature and high crystallinity, whereas MCL-PHAs are elastomeric in nature and have a low melting temperature and low crystallinity.

Poly(3-hydroxybutyrate), commonly referred to as "P(3HB)", is one of the most extensively studied SCL-PHAs. However, one of the major hindrances in the extensive commercial use of P(3HB) is its brittle and rigid nature owing to its high crystallinity. Poly(3-hydroxyoctanoate) or "P(3HO)" is one of the most extensively studied MCL-PHAs, but this similarly has not yet been commercially exploited due to its low melting temperature and tensile strength.

Depending on the nature of the application, desired properties can be achieved by making blends of PHAs and/or composites with organic and inorganic additives. Polymer blends may be miscible (homogeneous), immiscible (heterogeneous), or partially miscible (compatible) in nature. Most polymers are immiscible with other polymer materials and undergo phase separation when physically blended.

When producing any blend of two or more polymer materials, it can be difficult to predict the properties of the resulting blend due to the formation of multiphase polymer systems. The properties of such systems are determined not only by the constituent components but, to a large extent, by the morphology of the multiphase system. Therefore properties of any polymer blend made by physical blending are difficult to predict. The interaction between the components of the blend can lead to enhanced properties, but equally may lead to no change in properties or, in some cases, less desirable properties. Such properties can include mechanical, thermal and morphological properties.

PHAs possess great potential as materials for use in the manufacturing of nerve guidance conduits to assist axonal regeneration due to their properties, such as controllable surface erosion, lower acidity of their degradation products, and longer stability compared to their synthetic counterparts. P(3HB) and P(3HB-co-3HHx) have been explored for their use in nerve regeneration. For example, P(3HB) conduits have been shown to repair nerve gaps of 10 mm and 40 mm in rat sciatic nerves and rabbit peroneal nerves, respectively (see Hart et al., Br. J. Plast. Surg. 56: 444-450, 2003; Hazari et al., Br. J. Plast. Surg. 52: 653-657, 1999; Mosahebi et al., Glia. 34: 8-17, 2001; Mosahebi et al., Exp. Neurol. 173: 213-223, 2002; Mosahebi et al., Tissue Eng. 9: 209-218, 2003; Mohanna et al., Scand. J. Plast. Reconstr. Surg. Hand Surg. 39: 129-137, 2005; and Young et al., Br. J. Plast. Surg. 55: 235-240, 2002). Hollow P(3HB-co-3HHx) conduits have also been used to bridge 10 mm defects in rat sciatic nerves (Bian et al., Biomaterials 30: 217-225, 2009). Although these studies showed low levels of inflammatory infiltration and suitable reabsorption time for nerve repair, the regeneration obtained was inferior to that obtained when using autologous nerve grafting.

More recently, P(3HB) and P(3HO) blends have been investigated for their use as bioresorbable biomaterials in the manufacture of nerve guidance conduits (Lizarraga-Valderrama et al., Engineering in Life Sciences 15(6): 612-621, 2015). Mechanical, physical and chemical properties of the blends were characterised and the biocompatibility of the materials with NG108-15 neuronal cells was also studied. All of the tested blends were compatible with NG108-15 neuronal cells, however the 25:75 P(3HO)/P(3HB) blend showed significantly better support for the growth and differentiation of these cells.

A need still exists for alternative polymer materials which are suitable for the production of nerve guidance conduits (NGCs), in particular such materials which can provide the required resistance and elasticity that NGCs require for adequate strength and flexibility at the site of implantation, and which can act as suitable physical scaffolds and guides for axonal regrowth. Such polymer materials should also exhibit desirable properties such as biocompatibility and biodegradability.

SUMMARY OF THE INVENTION

We have now found that nerve guidance conduits having desirable properties and, in particular, desirable mechanical properties such as tensile strength, elastic modulus and elasticity, can be produced using certain polymer blends containing PHA materials ("PHA blends"). These blends include at least one PHA polymer which is a PHA copolymer comprising two or more different medium chain length hydroxyalkanoate (HA) repeating units. These particular PHA blends have not been previously produced, nor has their use in the production of nerve guidance conduits been previously suggested.

In one aspect the invention relates to a nerve guidance conduit having a body which comprises a polymer blend comprising:
  (a) from 60 to 98 wt. % of a first component which is a PHA copolymer comprising two or more different medium chain length hydroxyalkanoate monomer units; and
  (b) from 2 to 40 wt. % of a second component which is either a PHA homopolymer containing a short chain length hydroxyalkanoate monomer unit, or a polylactide (PLA).

In another aspect the invention relates to a method of producing a nerve guidance conduit having a body which comprises a polymer blend, said method comprising forming said body from a polymer blend which comprises:
  (a) from 60 to 98 wt. % of a first component which is a PHA copolymer comprising two or more different medium chain length hydroxyalkanoate monomer units; and
  (b) from 2 to 40 wt. % of a second component which is either a PHA homopolymer containing a short chain length hydroxyalkanoate monomer unit, or a polylactide (PLA).

In a further aspect the invention relates to a polymer blend comprising:
  (a) from 60 to 98 wt. % of a first component which is a PHA copolymer comprising two or more different medium chain length hydroxyalkanoate monomer units; and
  (b) from 2 to 40 wt. % of a second component which is either a PHA homopolymer containing a short chain length hydroxyalkanoate monomer unit, or a polylactide (PLA).

In a yet further aspect the invention relates to a method of producing a PHA copolymer, said method comprising the steps of:
  (a) culturing *Pseudomonas mendocina* CH50 in a culture medium comprising a carbon source other than glucose;
  (b) harvesting biomass from the culture medium;
  (c) extracting PHA from the harvested biomass; and
  (d) optionally purifying the crude PHA whereby to obtain a purified PHA.

In yet another aspect the invention provides a PHA copolymer obtained or obtainable by culturing *Pseudomonas mendocina* CH50 in the presence of a culture medium which comprises a carbon source other than glucose.

DETAILED DESCRIPTION OF THE INVENTION

Nerve guidance conduits comprising PHA blends are provided. In at least some aspects the PHA blends herein described have one or more properties, particularly mechanical properties, which are enhanced relative to the same properties of each of the individual blend components. In at least some embodiments, one or more properties, especially mechanical properties, of the PHA blends herein described are enhanced relative to the same properties of the major component of the blend, i.e. the first component (component (a)).

Definitions

As used herein, the term "polymer" refers to a molecular chain of repeating units that may be linear or branched. It includes homopolymers and copolymers.

The term "homopolymer" as used herein refers to a polymer with a single repeating unit. The term "copolymer" as used herein refers to a polymer with at least two different repeating units.

As used herein, the term "monomer" means a repeating unit of a polymer. The term "comonomer" refers to one of a least two monomers that are present in a copolymer.

As used herein, the term "polyhydroxyalkanoate" (or "PHA") refers to a biodegradable polyester which is synthesised by a microorganism.

The term "PHA homopolymer" as used herein refers to a polymer with a single hydroxyalkanoate (HA) repeating unit. The term "PHA copolymer" as used herein refers to a polymer comprising two or more different hydroxyalkanoate (HA) repeating units.

Reference herein to a "short chain length PHA" (or "SCL-PHA") means a PHA having 3 to 5 carbon atoms in its repeating units. A "medium chain length PHA" (or "MCL-PHA") means a PHA having more than 5 carbon atoms in its repeating units. The terms "short chain length hydroxyalkanoate monomer unit" and "medium chain length hydroxyalkanoate monomer unit" should be construed accordingly.

The term "poly(3-hydroxyalkanoate)" (or "P(3HA)") as used herein refers to a polymer in which each repeating unit comprises three carbons in the backbone. Any remaining carbons are in the side-chain. For example, "poly(3-hydroxybutyrate)" (or "P(3HB)") means a homopolymer comprising 3-hydroxybutyrate units in which three carbon atoms of each unit are present in the backbone and one carbon atom in each unit is in the side-chain. The term "P(3HA)" may be used generally to refer to a homopolymer or a copolymer.

As used herein, "polylactic acid" or "polylactide" means a homopolymer of lactic acid units. It may also be referred to as "PLA". The term "PLLA" refers to poly-L-lactic acid in which each of the lactic acid units has the L-configuration.

As used herein, "glass transition temperature" (Tg) is the temperature at which the amorphous domains of a polymer change from a relatively brittle vitreous state to a solid deformable or ductile state. Tg thus corresponds to the temperature at which the onset of segmental motion in the polymer chains occurs.

As used herein, the "melting temperature" (Tm) of a polymer is the temperature at which the polymer changes from a solid to a liquid state, i.e. the peak temperature at which a semi-crystalline phase melts into an amorphous phase.

As used herein, the term "polymer blend" is generally used to refer to a physical combination of two or more polymer components as opposed to a chemical combination in which monomer units of a polymer are chemically linked. A "PHA blend" refers to a physical combination of different polymers, at least one of which is a PHA polymer.

An "immiscible blend" refers to a blend having composition-independent Tg(s) and Tm(s). The observed Tg(s) and Tm(s) of the immiscible blend are about the same as those of the individual components of the blend. The number of Tg(s) and Tm(s) of an immiscible blend is the same as the number of components of the blend, e.g. a two component PHA blend will exhibit two composition-independent Tg(s) and two composition-independent Tm(s).

As used herein, "tensile strength" is a measure of the capacity of a material to withstand a loading tending to elongate it. It is the maximum tensile stress which a material will withstand prior to fracture. The ultimate tensile strength is the maximum load applied during a test divided by the original cross-sectional area of the sample.

As used herein, any reference to "elasticity" or "Young's modulus" is a measure of the stiffness of a material. It is the ratio of a component of stress or force per unit area applied to a material divided by the strain along an axis of applied force which results from the applied force. The modulus or the stiffness is generally the initial slope of the stress-strain curve at low strain, i.e. in the linear region.

As used herein, "elongation" of a material or "elongation at break" is a measure of the elastomeric properties of a material and is the amount of increase in length resulting from, for example, the tension to break the material. Generally it is expressed as a percentage of the original length of the material.

Tensile strength, Young's modulus and elongation at break may, for example, be determined according to the procedure in the examples presented herein using a 5942 Testing Systems (Instron) equipped with 500 N load cell at room temperature (20 to 25° C.).

Unless otherwise specified, as used herein "molecular weight" refers to weight average molecular weight (Mw) measured by Gel Permeation Chromatography (GPC) with polystyrene standards using, for example, chloroform as both the eluent and diluent for the samples. Calibration curves for determining molecular weights can be generated using polystyrene molecular weight standards. Weight average molecular weight is the sum of the products of the molecular weight of each polymer fraction multiplied by its weight fraction. GPC analysis can provide weight average molecular weight (Mw) and polydispersity index (PDI). Molecular weight (Mw) may, for example, be determined according to the procedure in the examples presented herein using a PLgel 5 µm MIXED-C (300×7.5 mm) column calibrated using narrow molecular weight polystyrene standards from 162 Da to 15,000 kDa.

As referred to herein, the polydispersity index (PDI) of a polymer is calculated by dividing the weight average molecular weight of the polymer by its number average molecular weight. The number average molecular weight can be measured using GPC, for example as herein described.

As used herein the term "biocompatible" refers to materials which are not toxic in vivo, and which do not elicit severe inflammatory or chronic responses in vivo. Degradation products (i.e. metabolites) of such materials should also be biocompatible. "Biodegradation" refers to the process of breakdown or dissolving of a material under physiological conditions, preferably in a period of less than 5 years, e.g. less than 2 years. It refers to a process which takes place in an animal, e.g. a human, and may occur by any suitable mechanism, such as hydrolysis. The biodegradation process via hydrolysis can occur with or without the presence of enzymes, such as lipases and other hydrolytic enzymes. The term "biodegradable", when used in respect of any of the materials herein described, should be construed accordingly.

The first component of the PHA blends herein described is a PHA copolymer comprising two or more different medium chain length HA units. The PHA copolymer thus comprises at least two hydroxyalkanoate comonomers, namely a first hydroxyalkanoate comonomer and a second hydroxyalkanoate comonomer, wherein said first and said second comonomers are different to one another.

In one embodiment, the PHA copolymer may include two different types of hydroxyalkanoate repeating units (a "binary" PHA copolymer). In another embodiment, the PHA copolymer may further comprise a third hydroxyalkanoate comonomer in which each of said first, second and third comonomers is different from each other (a "ternary" PHA copolymer).

The comonomers present in the PHA copolymer are medium chain length hydroxyalkanoates and each of these, independently of one another, contains 6 or more carbon atoms. In one embodiment these may each independently contain from 6 to 16 carbon atoms, preferably from 6 to 14 carbon atoms, more preferably from 8 to 12 carbon atoms, e.g. 8, 10 or 12 carbon atoms.

The position of the hydroxy group within each monomer unit in the PHA copolymer may vary independently of one another, but typically these will be present at C-3, C-4, C-5 or C-6. In one embodiment the first, second and, where present, third comonomers can be independently selected from any medium chain length 3-hydroxy and 4-hydroxyalkanoates. The PHA copolymer may, for example, comprise both 3-hydroxyalkanoate and 4-hydroxyalkanoate units although, more typically, it will consist of either 3-hydroxyalkanoate or 4-hydroxyalkanoate units. Typically, each monomer unit will contain from 6 to 16 carbon atoms, preferably from 6 to 14 carbon atoms, more preferably from 8 to 12 carbon atoms, e.g. 8, 10 or 12 carbon atoms.

In one embodiment, the first, second and, where present, third comonomer units in the PHA copolymer will be a medium chain length 3-hydroxyalkanoate (3HA). These may contain from 6 to 16 carbon atoms, preferably from 6 to 14 carbon atoms, more preferably from 8 to 12 carbon atoms, e.g. 8, 10 or 12 carbon atoms. Suitable examples of 3HAs which may be present include those selected from the group consisting of 3-hydroxyoctanoate (3HO), 3-hydroxydecanoate (3HD) and 3-hydroxydodecanoate (3HDD).

In one embodiment the PHA copolymer is poly(3-hydroxyoctanoate-co-3-hydroxydecanoate), also referred to herein as "P(3HO-3HD)" or "P(3HO-co-3HD)". This has the following structure:

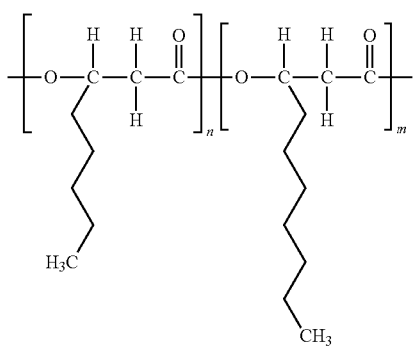

(I)

wherein n and m represent the number of repeating units of the 3HO and 3HD comonomers, respectively. In formula (I), n may range from about 300 to about 600, preferably from about 400 to about 500, e.g. about 450. In one embodiment, n may be 470. m may range from about 1,000 to about 1,300, preferably from about 1,100 to about 1,200, e.g. about 1,150. In one embodiment, m may be about 1,165. In one embodiment of formula (I), n=470 and m=1,165.

In one embodiment the PHA copolymer is poly(3-hydroxyoctanoate-co-3-hydroxydecanoate-co-3-hydroxydodecanoate), also referred to herein as "P(3HO-3HD-3HDD)" or "P(3HO-co-3HD-co-3HDD)". This has the following structure:

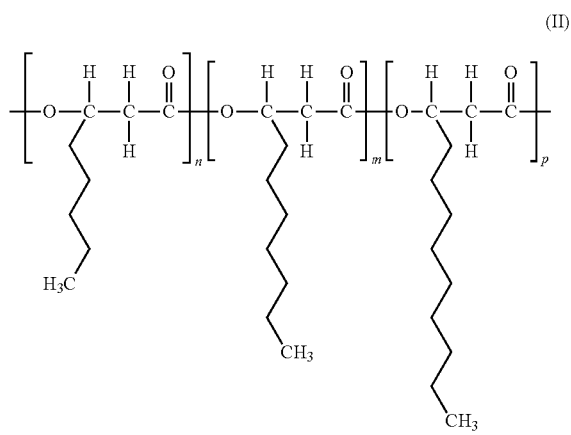

(II)

wherein n, m and p represent the number of repeating units of the 3HO, 3HD and 3-HDD comonomers, respectively. In formula (II), n may range from about 450 to about 800, preferably from about 550 to about 700, e.g. about 650. In one embodiment, n may be 630. m may range from about 700 to about 1,000, preferably from about 800 to about 900, e.g. about 850. In one embodiment, m may be about 860. p may range from about 200 to about 500, preferably from about 250 to about 400, e.g. about 350. In one embodiment, p may be 325. In one embodiment of formula (II), n=630, m=860, and p=325.

The chirality of the hydroxy-substituted carbon atom in each HA unit will be determined by the stereospecificity of the PHA biosynthetic enzymes used in the preparation of the polymer materials and will generally be of the R-configuration. Accordingly, the first blend component will preferably consist of R-hydroxyalkanoic acid monomers, e.g. R-3-hydroxyalkanoic acid monomers.

The PHA copolymer may include random or alternating repeating monomer units dependent on the method used for its production. Typically, however, it will be a random copolymer.

The molar ratio of comonomer units in the PHA copolymer may vary and will be dependent on the method used to produce the polymer. For example, the molar ratio will be determined by factors such as the type of microorganism and the biosynthetic pathway which it adopts to produce the copolymer, the nature of the feedstock used in its production, for example the carbon source and its concentration, the carbon source feeding strategy, the carbon to nitrogen ratio employed during biosynthesis, and other culturing process parameters.

In one embodiment, the PHA copolymer will contain 3-hydroxydecanoate (3-HD) monomer units and these will be present as the major component of the polymer. For example, where the PHA copolymer is a binary copolymer, the 3-hydroxydecanoate monomer units may be present in an amount ranging from 60 mol % to 85 mol %, preferably from 65 to 85 mol %, more preferably from 70 to 80 mol %, e.g. from 72 to 76 mol % (based on the weight average molecular weight, Mw, of the PHA copolymer). Where the PHA copolymer is a ternary copolymer, the 3-hydroxydecanoate monomer units may, for example, be present in an amount ranging from 40 mol % to 60 mol %, preferably from 40 to 55 mol %, more preferably from 45 to 55 mol %, e.g. from 47 to 50 mol % (based on the weight average molecular weight, Mw, of the PHA copolymer). High amounts of 3-hydroxydecanoate (3-HD) may be produced during the biosynthesis of MCL-PHAs by appropriate selection of the microorganism. For example, *Pseudomonas* species, such as *Pseudomonas mendocina* CH50, *Pseudomonas putida* LS46 and *Pseudomonas putida* KT2440, may be used to produce 3-hydroxydecanoate in high amounts in a PHA copolymer as herein described.

In one embodiment, the PHA copolymer will contain 3-hydroxyoctanoate (3-HO) monomer units. This may be present in an amount ranging from 15 to 40 mol %, preferably from 20 to 35 mol %, more preferably from 25 to 35 mol % (based on the weight average molecular weight, Mw, of the PHA copolymer). Where the PHA copolymer is a binary polymer, the 3-hydroxyoctanoate monomer units may be present in an amount from 20 to 35 mol %, preferably 20 to 30 mol %, e.g. from 24 to 28 mol % (based on the weight average molecular weight, Mw, of the PHA copolymer). Where the PHA copolymer is a ternary polymer, the 3-hydroxyoctanoate monomer units may be present in an amount from 20 to 40 mol %, preferably 25 to 35 mol %, e.g. from 30 to 35 mol % (based on the weight average molecular weight, Mw, of the PHA copolymer).

In one embodiment, the PHA copolymer will contain 3-hydroxydodecanoate (3-HDD) monomer units. This may be present in an amount ranging from 10 to 30 mol %, preferably from 15 to 25 mol %, e.g. 17 to 22 mol % (based on the weight average molecular weight, Mw, of the PHA copolymer). Where such monomer units are present, the PHA copolymer will generally be a ternary polymer.

Molecular weight ranges for the MCL-PHA copolymers will be dependent on the method used in their production and may be adjusted accordingly. For example, the molecular weight will be determined by factors such as the type of microorganism and the biosynthetic pathway which it adopts to produce the PHA copolymer, the nature of the carbon source, process parameters, etc. Suitable molecular weights may range from 50 to 600 kDa, preferably from 150 to 500 kDa, more preferably from 200 to 400 kDa, e.g. from 200 to 350 kDa or from 300 to 350 kDa. In one embodiment, the molecular weight of the PHA copolymer may be about 330 to about 340 kDa.

The second component of the polymer blends is either a PHA homopolymer containing short chain length hydroxyalkanoate monomer units, or a polylactide (PLA).

In one embodiment the second component of the blend is a PHA homopolymer containing a short chain length PHA unit. The short chain length PHA may have 3, 4 or 5 carbon atoms in the repeating unit. Preferably this will have 3 carbon atoms in the repeating unit.

In one embodiment the PHA homopolymer is poly(3-hydroxybutyrate) or "P(3HB)" which is a homopolymer of 3-hydroxybutyric acid units. P(3HB) has the following structure:

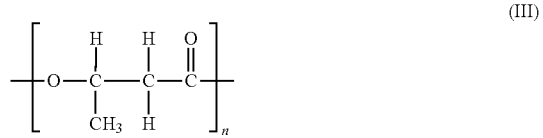

(III)

wherein n represents the number of repeating units of the 3HB monomer. In formula (III), n may range from about 3,000 to 23,000, preferably from about 3,400 to about 22,700, e.g. about 5,800 to about 11,600.

Molecular weight ranges for the SCL-PHA polymer will be dependent on the method used in their production and may be adjusted accordingly. For example, the molecular weight will be determined by factors such as the type of microorganism and the biosynthetic pathway which it adopts to produce the PHA homopolymer, the nature of the carbon source, process parameters, etc. Suitable molecular weights may range from 200 kDa to 2 MDa, preferably from 300 kDa to 2 MDa, e.g. from 350 kDa to 1 MDa, from 500 kDa to 1 MDa, or from 350 kDa to 500 kDa.

In another embodiment the second component may be a polylactide comprising lactic acid repeating units. Poly (lactic acid) or "PLA" is a biodegradable semi-crystalline polyester which may exist in different stereoisomeric forms: L- and D-lactic acid. For use in the invention, the PLA may take any suitable form selected from poly(L-lactic acid) ("PLLA"), poly(D-lactic acid) ("PDLA"), and racemic products, i.e. poly(D,L-lactide). Preferred for use in the invention is PLLA.

PLA polymers are available commercially from suppliers such as CORBION, GoodFellow, and Sigma. Those which are commercially available may have molecular weights as follows: PLLA—100 kDa to 260 kDa; PLDA—about 124 kDa; PDLA 10 to 28 kDa. In one embodiment the PLA polymer is PL38 PURASORB which is a homopolymer of L-lactic acid supplied by Corbion (Netherlands).

The PHA blends for use in the invention comprise: (a) from 60 to 98 wt. % of a first component which is a PHA copolymer comprising two or more different medium chain length HA monomer units; and (b) from 2 to 40 wt. % of a second component which is either a PHA homopolymer containing a short chain length hydroxyalkanoate monomer unit, or a polylactide (PLA). Any combination of any of the first and second blend components herein described may provide a PHA blend for use in the invention. Such PHA blends are in themselves novel and any of the blends herein described form a further aspect of the invention.

In one embodiment the PHA blend may comprise a first component which is a PHA copolymer comprising two or more different medium chain length HAs, and a second component which is poly(3-hydroxybutyrate) (or "P(3HB)").

In another embodiment the PHA blend may comprise a first component which is selected from poly(3-hydroxyoctanoate-co-3-hydroxydecanoate) (or "P(3HO-3HD)") and poly(3-hydroxyoctanoate-co-3-hydroxydecanoate-co-3-hydroxydodecanoate) (or "P(3HO-3HD-3HDD)"), and a second component which is poly(3-hydroxybutyrate) (or "P(3HB)").

In one embodiment the PHA blend may comprise a first component which is a PHA copolymer comprising two or more different medium chain length HAs, and a second component which is a polylactide.

In another embodiment, the PHA blend may comprise a first component which is selected from poly(3-hydroxyoctanoate-co-3-hydroxydecanoate) (or "P(3HO-3HD)") and poly(3-hydroxyoctanoate-co-3-hydroxydecanoate-co-3-hydroxydodecanoate) (or "P(3HO-3HD-3HDD)"), and a second component which is a polylactide.

Non-limiting examples of suitable PHA blends include the following:
P(3HO-3HD)/P(3HB)
P(3HO-3HD-3HDD)/P(3HB)
P(3HO-3HD-3HDD)/PLA
P(3HO-3HD)/PLA
P(3HO-3HD-3HDD)/PLLA
P(3HO-3HD)/PLLA
P(3HO-3HD-3HDD)/PDLA
P(3HO-3HD)/PDLA The first component forms the major component of the blend and is present in an amount ranging from 60 to 98 wt. % (based on the total weight of the blend). More specifically, this may be present in an amount ranging from 65 to 96 wt. %, preferably from 70 to 95 wt. %, more preferably from 75 to 90 wt. %, e.g. from 80 to 85 wt. %. Where the second component is a PHA homopolymer, the amount of the first component may range from 70 to 90 wt. %, preferably from 75 to 85 wt. %, e.g. about 85 wt. %. Where the second component of the blend is a polylactide, the amount of the first component may range from 80 to 98 wt. %, preferably from 85 to 97 wt. %, more preferably from 90 to 96 wt. %, e.g. about 95 wt. %.

The second component forms the minor component of the blend and is present in an amount ranging from 2 to 40 wt. % (based on the total weight of the blend). More specifically, this may be present in an amount in the range from 5 to 35 wt. %, preferably from 10 to 30 wt. %, more preferably from 15 to 25 wt. %, e.g. from about 15 to 20 wt. %. Where the second component of the blend is a PHA homopolymer, this may be present in an amount in the range from 10 to 30 wt. %, preferably 15 to 25 wt. %, e.g. about 15 wt.%. Where the second component of the blend is a polylactide, this may be present in an amount in the range from 2 to 15 wt. %, preferably 3 to 10 wt. %, e.g. about 5 wt. %.

In one embodiment of the invention the PHA blends are binary blends containing only the first and second polymer components herein defined. In other embodiments, however, these may contain other known components such as other polymers, fillers or additives as desired. Other biodegradable polymers which may be present include polysaccharides such as cellulose and its derivatives (e.g. hydroxypropylcellulose, methylcellulose, cellulose acetate, etc.), starch and its derivatives, chitosan, alginate, hyaluronic acid, pectin, carrageenans, agarose, and chondroitin sulphate; proteins such as collagen, gelatine, elastin, albumin, fibrin, and natural polyamino acids (e.g. poly-glutamic acid, poly-lysine, etc.);

synthetic polyesters such as polydioxanone, poly(trimethylene carbonate); polyurethanes; poly(ester amide)s; polyanhydrides; poly(anhydride-co-imide); polyphosphazenes; and polyphosphoesters. Fillers or additives which may be present include plasticizers (e.g. fatty acids, soybean oil, sorbitol, PEG, oleic acid, citric acid, tartaric acid, malic acid, etc.), and stiffening or reinforcing agents such as synthetic and natural clay minerals, graphene and its derivatives, carbon nanotubes, silica, hexagonal and tubular boron nitride, double layered hydroxides, polyhedral oligomeric silsesquioxane (POSS), monocrystalline and nanofibrillated cellulose, starch, chitosan, bioactive glass, and phosphate glass. Fillers can be introduced as reinforcing additives to change the mechanical properties and/or as modifiers of the kinetics for the release of any active agents.

Other components which may be present include electrically conductive substances such as polyaniline, carbon nanotubes, graphene, graphene oxide, etc.

Bioactive agents may also be present and include growth factors which may enhance the response of seeded cells or the cells near the defect site. These may, for example, be employed to promote neuronal survival and stimulate neurite outgrowth following trauma. The ability to combine neurotrophic factor delivery with a neural conduit can support, promote, and direct neurite outgrowth.

Examples of bioactive agents which may be present include, but are not limited to, any of the following and combinations thereof:

Nerve growth factor (NGF)—NGF can ensure the survival of the cells and support the regeneration of the axons toward specific target organs; it is critical for the survival and maintenance of sympathetic and sensory neurons.

Brain-derived neurotrophic factor (BDNF)—this helps to support the survival of existing neurons, and encourage the growth and differentiation of new neurons and synapses through axonal and dendritic sprouting.

Neurotrophin-3 (NT-3)—NT-3 is a neurotrophic factor that has activity on certain neurons of the peripheral and central nervous system. It helps to support the survival and differentiation of existing neurons, and encourages the growth and differentiation of new neurons and synapses.

Glial cell-line derived neurotrophic factor (GDNF)—GDNF is a small protein that potently promotes the survival of many types of neurons.

Fibroblast growth factors (FGF)—these promote neuronal survival and stimulates axonal growth.

Ciliary neurotrophic factor (CNTF)—this promotes neurite growth from NGF responsive sensory and sympathetic neurons, supporting the survival of motoneurons.

Platelet-derived growth factor (PDGF)—this regulates cell growth and division, which plays a significant role in blood vessel formation (angiogenesis). It is a potent mitogen for glial cells.

Vascular endothelial growth factor (VEGF)—VEGF can protect damaged neurons or nerve after cerebral ischemia or spinal cord injury. It has beneficial effects on neurone survival and Schwann cell proliferation. VEGF is a potent angiogenic factor, and angiogenesis has been recognized as a necessary step during tissue repair.

Glial growth factor (GGF)—GGF is a trophic factor specific for Schwann cells which are not only important for neuronal survival and axonal specialization during development, but are essential for axonal regrowth following injury.

Sabeluzole—a benzothiazole derivative which is a nootropic and neuroprotective drug which ensures the stability of the neuronal cytoskeleton.

Inosine—a purine analog which capable of promoting axonal extension following neural injury.

Tirofiban (TF)—a non-peptide RGD-mimetic molecule which is an anti-thrombotic (antiplatelet) drug. It belongs to the class of glycoprotein IIb/IIIa inhibitors.

Extracellular matrix components such as fibronectin, laminin and collagen—these serve to promote cell adhesion to the surface of the nerve conduit.

RGD peptide—this contains L-arginine, glycine, and L-aspartic acid (Arg-Gly-Asp). It is a cell adhesion molecule which mediates peripheral neuron regeneration.

Schwann cells—these are normally present in the neural cells and serve to keep the peripheral nerve fibres alive. Schwann cells promote neural regeneration and remyelination. They also function to provide support and guidance to the regenerating axons.

PHAs suitable for use in the invention and methods for their production are generally known in the art. The PHAs can be prepared from a biological source such as a microorganism which naturally produces PHAs and which can be induced to produce the desired PHAs by adjusting the culture conditions and feedstocks. PHAs may be produced in natural or genetically engineered microorganisms.

PHAs are derived from microorganisms, typically from bacteria, by culturing in a bioreactor under conditions in which the supply of nutrients is limited. In such methods, a culture of the microorganism in a suitable medium is fed appropriate nutrients so that it multiplies rapidly. Once the microorganism has multiplied to a sufficient level, the nature of the nutrient composition is changed to force the microorganism to synthesise PHA. Biosynthesis of PHAs may be induced by limiting the supply of nutrients such as phosphorus, nitrogen, and trace elements, by reducing the supply of oxygen, or by an excess supply of carbon sources. The PHAs are deposited in the form of highly refractive granules in the cells and can be recovered by disruption of the cells.

The choice of different carbon sources, feeding strategies, media compositions and bacterial strains will ultimately define the final type of polymer and can be adjusted accordingly. Metabolic preferences of any given strain towards carbon sources and thus the production of certain PHAs are generally known in the art or can readily be determined by those skilled in the art. For example, when using *Pseudomonas* sp, the use of a structurally related carbon source, such as octanoic acid, typically results in the production of either a P(3HO) homopolymer or a P(3HO-3HD) copolymer, with 3HO present in the greater amount. On the other hand, the use of an unrelated carbon source (e.g. glucose) forces the microorganism to undergo a different metabolic pathway and produce different MCL-PHA monomer units. For any given bacterial strain, adjustment of the media composition, feeding strategies and/or growth conditions can be used to tailor the composition of the PHA product including the ratio of monomers in any resulting copolymer.

Any strain of bacteria known in the art that produces PHAs can be used for producing the PHAs for use in the invention. Various microorganisms are known for use in the production of PHAs. This includes both Gram-negative and Gram-positive bacteria, although Gram-negative bacteria are mainly used. Those generally used for the production of short-chain length PHAs (SCL-PHAs) include *Cupriavidus necator* (formerly known as *Ralstonia eutropha*), *Alcaligenes latus*, *Bacillus cereus*, *Aeromonas caviae*, *Rho-*

*dospirillum rubrum, Methylobacterium extorquens, Halomonas boliviensis* LC1, *Bacillus subtilis*, and *Bacillus megaterium*. Those typically used for the production of medium-chain length PHAs (MCL-PHAs) and their copolymers include those of *Pseudomonas* genus, for example *Pseudomonas putida, Pseudomonas oleovorans, Pseudomonas mendocina* CH50, *Pseudomonas fluorescence, Pseudomonas aeruginosa, Pseudomonas raguenesii, Pseudomonas guezennei, Pseudomonas stutzeri*, and *Pseudomonas cepacia. Comamonas* species, such as *Comamonas testosteronii*, may also be used.

Suitable microorganisms for use in the invention are commercially available from various sources, such as NCIMB or ATCC.

In the production of SCL-PHAs, for example P(3HB), the use of the Gram-positive bacterium *Bacillus subtilis*, e.g. *Bacillus subtilis* OK2, has been found to be particularly beneficial. *Bacillus subtilis* OK2 is commercially available from various sources, e.g. from the National Institute of Genetics. It has also been deposited by the Applicant at the National Collection of Industrial and Marine Bacteria (NCIMB), which serves as an International Depositary Authority (IDA), on 1 Sep. 2017, under accession number NCIMB 42804. *Bacillus subtilis* is classified as GRAS. As a Gram-positive bacterium it also lacks lipopolysaccharides (LPS) and thus the polymer produced will lack LPS, which is a strong immunogen, and hence be inherently non-immunogenic. It has been found to provide SCL-PHAs in good yield with a high molecular weight. Its use in the production of the PHA homopolymer (e.g. P(3HB)) represents a preferred embodiment of the invention.

*Pseudomonas mendocina* CH50 has been found to be particularly suitable for use in the invention for the production of MCL-PHAs, at least in part due to its versatility with respect to the choice of carbon source. Specifically, the inventors have found it has the ability to use a range of carbon sources for the production of PHAs other than glucose. Suitable carbon sources may include vegetable oils, carbohydrates, and fatty acids, as well as sugarcane molasses and biodiesel waste. The use of *Pseudomonas mendocina* CH50 to produce PHA copolymers as herein described using a carbon source other than glucose, and the resulting PHA copolymers form further aspects of the invention.

In another aspect, the invention thus provides a method of producing a PHA copolymer, preferably a PHA copolymer comprising two or more different medium chain length HAs (e.g. P(3HO-3HD) or P(3HO-3HD-3HDD)), said method comprising the steps of: culturing *Pseudomonas mendocina* CH50 in a culture medium which includes a carbon source other than glucose; harvesting biomass from the culture medium; extracting PHA from the harvested biomass; and optionally purifying the crude PHA whereby to obtain a purified PHA.

In yet another aspect the invention provides a PHA copolymer, for example P(3HO-3HD) or P(3HO-3HD-3HDD), obtained or obtainable by culturing *Pseudomonas mendocina* CH50 in the presence of a culture medium which includes a carbon source other than glucose. The PHA copolymer may be a copolymer as herein defined in respect of any of the embodiments relating to the PHA blend.

Microorganisms may be cultured to produce PHAs using any conventional methods for bacterial cultivation, including batch-mode and continuous mode bioreactor cultivation. During culturing of the microorganisms the conditions are carefully controlled. This includes control over appropriate levels of nutrients, dissolved oxygen, temperature and pH. Required nutrients include carbon, nitrogen, and phosphorus as well as mineral salts. Suitable conditions for culturing may readily be determined by those skilled in the art taking into account considerations such as the nature of the microorganism and its optimum growth conditions. Typically, the pH will be in the range of from 6.0 to 7.0, preferably from 6.5 to 7.0, e.g. about 7.0. The temperature for culturing will typically range from about 30 to 35° C., for example it may be about 30° C. Mixing speeds and time of mixing should be sufficient to allow the microorganism to proliferate and to allow PHA to be synthesised. Suitable mixing speeds may be in the range from 150 to 200 rpm, e.g. about 200 rpm, and mixing times may range from about 12 to about 48 hours, e.g. about 48 hours.

The choice of nutrient media will be dependent, at least in part, on the choice of microorganism—this depends on the metabolic pathway used by the organism for PHA synthesis—but it will include both carbon and nitrogen sources, as well as salts and minerals and other trace elements.

The use of different carbon sources will define different monomer unit compositions within the polymer chain and thus the properties of the obtained PHA materials. Suitable carbon sources include any of the following, and any mixtures thereof:

Carbohydrates such as glucose, sucrose, fructose, galactose, arabinose and xylose, or mixtures thereof;

Lipids such as those derived from vegetable oils, coconut oil, walnut oil, corn oil, rapeseed oil, hazelnut oil, olive oil, groundnut oil, fish oil, etc. Examples of suitable lipids include $C_{6-18}$ fatty acids, preferably $C_{2-18}$ fatty acids, and their salts, e.g. hexanoic acid, heptanoic acid, octanoic acid, nonanoic acid, decanoic acid, undecanoic acid, dodecanoic acid, and their salts;

Alcohols such as ethanol, glycerol, n-propanol, n-butanol, 1,4-butane-diol, propylene glycol;

Organic acids such as acetate, propionate, butyrate, valerate, lactate, citrate, etc.

Amino acids, such as glutamate, histidine, asparagine, etc.

Waste materials such as by-products of biodiesel production (e.g. crude glycerol);

Complex carbohydrates, e.g. sugarcane molasses;

Yeast extract;

Other organic molecules such as γ-butyrolactone.

Mixtures of carbohydrates and fatty acids are generally preferred for use in production of the PHA polymer materials.

A preferred carbon source for use in the production of both SCL and MCL-PHAs is glucose. For the production of MCL-PHAs, for example using the bacterial strain *Pseudomonas mendocina* CH50, coconut oil is a preferred carbon source.

Suitable nitrogen sources include ammonium salts such as ammonium sulphate, ammonium chloride, and ammonium hydroxide, urea, and yeast extract.

PHA production generally involves a two-stage procedure—a first stage involving rapid cell growth followed by a second accumulation stage. The nature of the nutrient media for use in the different stages of the procedure will differ. Exhaustion of one or more types of nutrients in the second stage results in the accumulation of PHAs. The use of nitrogen-limiting conditions may be used to force the organism to use the carbon source and synthesise PHAs.

For the production of SCL-PHAs, a modified Kannan and Rehacek media (K-R) may be used (see Kannan LV and Rehacek Z, Indian J. Biochem. 7: 126-129, 1970). This has the following composition (g/L): ammonium sulphate 5.0, potassium chloride 3.0, yeast extract 2.5, glucose 35.0.

A suitable production medium for use in the production of MCL-PHAs is a Mineral Salt Medium (MSM). This may be used in a two-stage culture as follows:

MSM media composition (first stage) (g/L): ammonium sulphate 0.45, potassium phosphate monobasic 2.38, sodium hydrogen phosphate 3.42, magnesium sulphate 0.4, carbon source 20.0, trace elements 1 mL/L.

MSM media composition (production stage) g/L: ammonium sulphate 0.50; potassium phosphate monobasic 2.65; sodium hydrogen phosphate 3.80; magnesium sulphate 0.4, carbon source 20.0, trace elements 1 mL/L.

An example of a trace element solution for use in the culture medium is (amounts provided in g/L): cobalt (II) chloride 0.22; iron (III) chloride 9.70; calcium chloride 7.80; nickel(III) chloride 0.12; chromium (VI) chloride 0.11; copper sulphate pentahydrate 0.16.

The monomeric composition and the molecular weight of the PHA materials can be controlled by complying with an established culturing protocol.

PHA is produced by disrupting the cells followed by extraction of the PHA from the disrupted cells. Standard methods known in the art can be used to disrupt the cells and release the PHAs produced, for example this may be done mechanically (e.g. by homogenisation), or chemically (e.g. by the addition of sodium hypochlorite). Collection of the biomass may be carried out using methods such as centrifugation which results in the formation of cell pellet. The harvested biomass is then washed, e.g. with water and frozen under standard conditions, e.g. at −20° C. before lyophilisation. For extraction and purification of PHA methods known in the art can be used. For example, the lyophilised cell mass may be mixed with an organic solvent such as chloroform, methylene chloride, or pyridine in order to extract the PHA using a soxhlet based extraction carried out at the boiling point of the solvent. Chloroform is generally preferred (boiling point: 65° C.). The polymer solution may be concentrated by standard methods such as rotary evaporation. The polymer can be precipitated from this solution using standard methods, for example the PHA solution may be added to cold organic solvent, such as methanol, ethanol, acetone, ether or hexane. The use of cold methanol is generally preferred. The polymer can be collected and, if desired, washed with additional solvent, e.g. methanol.

Extraction of PHA via the soxhlet method may, for example, be carried out as follows: after 48 hours of incubation, the cells are harvested by centrifugation at 4600 rpm for 30 minutes. The cell pellet is lyophilised prior to the extraction. Dried biomass is placed in a thimble within the soxhlet apparatus and refluxed for 24 hours with methanol at 70° C. This step is carried out to remove all the impurities soluble in methanol. Methanol is then replaced with chloroform, and the cells are refluxed for another 24 hours to facilitate PHA dissolution in the chloroform solution at 65° C. The chloroform solution is concentrated using a rotary evaporator. PHA is precipitated out using an ice cold solution of methanol.

Suitable lactic acid polymers for use in the invention are generally known in the art and are commercially available. These include PL38 which is a medical grade PLLA available from Corbion.

The PHA blends herein described are immiscible blends. These may be prepared using any of the conventional processes used in the plastics industry, including but not limited to, any of the following: melt blending using extrusion or blending in solutions. Blending in solution is generally preferred in order to retain the property of the materials. Processing temperatures will be dependent on the thermal properties of the blend components and can be selected accordingly. If using melt blending techniques, care should be taken to optimise the process to minimise the exposure of the materials to elevated temperatures since this can lead to deterioration of the materials' properties. The temperature for melt blending is defined by the melt temperature of the component in the blend having the highest melting temperature. In the blends herein described, the P(3HB) and PLA (e.g. PLLA) will typically have the highest melting temperatures (Tm about 175° C.). Suitable temperatures for melt blending may be in the range from 190 to 200° C.

Blending in solution may be carried out by adding the desired quantities of blend components to an organic solvent, such as chloroform, and stirring the solution to dissolve the polymer materials. Temperature and duration of stirring will depend on the nature of the blend components (e.g. their viscosity) and may readily be determined. For example, the temperature may range from 20 to 100° C., e.g. from 20 to 50° C. In one embodiment, blending may be carried out at ambient temperature. Stirring may be carried out for about 10 to 60 minutes, or longer (e.g. overnight). The duration of stirring will depend on the temperature and concentration of the components of the blend and may be shortened by blending at a higher temperature. Evaporation of the solvent results in precipitation of a PHA polymer blend. This may be filtered and dried, e.g. under vacuum conditions at elevated temperature.

The nerve guidance conduit may be any known design. Typically, the body of the NGC will be cylindrical. In certain embodiments, it may be hollow (i.e. tubular). The inner diameter of the conduit and its wall thickness may vary. For example, the inner diameter may vary from about 1 mm to about 10 mm. Wall thickness may range from about 0.5 mm to about 2 mm.

The blends herein described may be processed into a nerve guidance conduit or component thereof (e.g. a nerve conduit body or scaffold) using known manufacturing processes. Processes for producing a generally cylindrical scaffold body include injection moulding, extrusion, dip moulding using polymer solutions, film casting from polymer solutions, electrospinning, compression moulding, photochemical etching, lithography, and fused deposition modelling. Techniques such as extrusion and dip moulding from polymer solutions are particularly suitable for the production of hollow, thin-walled structures. 3D printing techniques may also be used.

Tubular forms of the conduit may include both dense, non-porous tubes and porous tubes. Porous structures contain a plurality of pores for permitting fluids and nutrients to pass through the body of the guidance channel to reach the internal lumens. In this manner, Schwann cells and regenerative nerve tissue within the internal lumens are able to receive nutrients and oxygen during nerve regeneration. It is preferable for the pores to be sized to inhibit the growth of regenerative nerve tissue through the pores.

Porous structures may be produced using methods known in the art, for example using pore-forming agents. A particulate leaching process using a porogen may, for example, be used. In such methods a pre-mix comprising the polymer blend and a porogen may be prepared and either extruded to produce a tube, dip moulded using a mandrel of suitable size and a polymer solution of optimised concentration and/or viscosity, or loaded into a mould having the desired geometry. Porous tubes may be provided by immersing the extruded tube or the mould carrying a moulded tube in water in order to wash out the porogen. Examples of suitable porogens include powdered sodium chloride, sucrose, glucose and maltodextrin. The porosity of such materials is determined by the fraction of porogen and may vary, for example, from about 5 to about 75 wt %.

Alternatively, porous NGCs can be produced by a gel extrusion method. In this method a polymer blend is dissolved in a poor solvent or a mixture of good and poor solvents at elevated temperature to achieve a solution of relatively high concentration. The polymer solution is extruded in a tubular shape and quickly gels on cooling due to the poor quality of the solvent. This induces a liquid/liquid demixing and the formation of two phases leading to the formation of a porous structure. Suitable poor solvents include, but are not limited to, any of the following: dioxane, dimethylsulfoxide, dimethylacetamide, dimethylformamide, isoamyl formate, isopentyl acetate, isoamyl propionate, dichloromethane, trichloroethane, and tetrachloroethane.

The nerve conduit may be sterilised using conventional methods such as gamma-radiation prior to final packaging ready for use.

The conduit of the invention is suitable for surgical implantation in the repair of a transected nerve. It may readily be cut to size according to the length of the nerve gap to be bridged in the repair and may be anchored in place with surgical sutures. In one embodiment, the invention also provides a method of regenerating a transected nerve across a nerve gap defined by a proximal end of the transected nerve and a distal end of the transected nerve. The method comprises suturing the proximal end of the transected nerve to a first end of a nerve guidance conduit as herein described, and suturing the distal end of the transected nerve to a second end of said nerve guidance conduit.

The PHA blends herein described have favourable properties for use in the production of nerve conduits. At least in some embodiments, such properties include one or more of the following:

High biocompatibility compared to established synthetic polymers.

The PHAs degrade by surface degradation and hence lead to long term stability of the implant compared to bulk degrading materials such as PLLA/PGA where the structure begins to loose stability due to bulk degradation.

The degradation products of PHAs are hydroxyalkanoic acids which are much less acidic than lactic acid/glycolic acid which are produced on degradation of PLLA/PGA implants and which cause inflammation.

The degradation products of PHAs are known metabolites already present in the body and hence are completely non-immunogenic in nature.

The degradation rate and mechanical properties of the PHA blends can be tailored to suit the patient condition.

The mechanical properties of the materials provide the desired flexibility properties such as elasticity. Mechanical properties include tensile strength which is a measure of the capacity of the material to withstand a loading tending to elongate it, Young's modulus which is a measure of the stiffness of a material, and elongation at break which is a measure of the elastomeric properties of a material.

In at least some embodiments, the tensile strength ($\sigma$) of the PHA blends herein described, as measured according to the method described in the examples, is greater than 0.1 MPa, preferably in the range of from 1 to 10 MPa.

In at least some embodiments, the Young's modulus (E) of the PHA blends herein described, as measured according to the method described in the examples, is greater than 0.5 MPa, preferably in the range of from 50 to 500 MPa.

In at least some embodiments, the elongation at break ($\varepsilon_b$) of the PHA blends herein described, as measured according to the method described in the examples, is at least 100%, preferably in the range from 200 to 600%. Elongation at break is particularly important due to the need for the nerve guidance conduit to stretch without breaking in situ.

Due to the limited compatibility of the components of the blends, their thermal properties will be similar to that of the components. On the other hand, mechanical properties are strongly dependent on the nature of the blend composition and can be tailored according to need, for example, by adjusting the ratio of first and second components, adjusting Mw/Mn of individual components, and adjusting the mol % of monomers in the PHA copolymer. The blends become more pliable and less stiff with an increase in the content of the first component.

EXAMPLES

The invention will now be described in more detail by way of the following non-limiting examples and with reference to the accompanying figures, in which:

FIG. 1 shows the $^1$H NMR (upper panel) and $^{13}$C NMR (lower panel) of the P(3HO-3HD) polymer produced by *P. mendocina* CH50 with glucose as the carbon source in Example 2.

FIG. 2 shows the $^1$H NMR (upper panel) and $^{13}$C NMR of the P(3HO-3HD-3HDD) polymer produced by *P. mendocina* CH50 with coconut oil as the carbon source in Example 3.

FIG. 3 shows the $^1$H NMR (upper panel) and $^{13}$C NMR (lower panel) of the P(3HB) polymer produced by *Cupriavidus necator* with walnut oil as carbon source in Example 8.

FIG. 4 shows the $^1$H NMR (upper panel) and $^{13}$C NMR (lower panel) of the P(3HO-3HD) polymer produced by *Pseudomonas mendocina* CH50 with sugarcane molasses as carbon source in Example 9.

Measurement of Mechanical Properties

In the following examples, tensile strength, Young's modulus and elongation at break are determined using a 5942 Testing Systems (Instron) equipped with 500 N load cell at room temperature. The test is conducted using films which are 5 mm in width and 3.5 to 5.0 cm in length. Before measurement, the thickness and width of the specimen are measured in several places and an average value used to calculate the cross-sectional area. The gauge length of the sample holder is set at 23 mm and a deformation rate of 5 mm per minute for SCL-PHA based materials and 10 mm per minute for MCL-PHA based materials is employed. Young's modulus, tensile strength and elongation at break are calculated from the stress-strain curve and average values calculated for 3-6 specimens. Data analysis is carried out using BlueHill 3 software.

Measurement of Molecular Weight

Unless otherwise specified, the molecular weight of the polymer materials is determined using a PLgel 5 μm MIXED-C (300×7.5 mm) column which is calibrated using narrow molecular weight polystyrene standards from 162 Da to 15,000 kDa. The eluent used was chloroform. 5 mg/mL of the polymer is introduced into the GPC system at a flow rate of 1 mL/min. The eluted polymer is detected with a refractive index detector. Data is collected and analysed using "Agilent GPC/SEC" software.

Example 1—Production and Characterisation of poly(3-hydroxybutyrate) "P(3HB)" from Glucose by *Bacillus subtilis* OK2

Producer Organism: *Bacillus subtilis* OK2 (Obtained from the National Institute of Genetics)
Media Composition:
Production Media
   Ammonium sulphate: 5 g/L
   Potassium chloride: 3 g/L
   Yeast extract: 2.5 g/L (autoclaved at 121° C. for 15 minutes)
Carbon Source
   Glucose: 35 g/L (autoclaved at 110° C. for 11 minutes)
   pH of all the media components was adjusted to 6.8
   Production: A single colony of *Bacillus subtilis* OK2 was used to inoculate the autoclaved nutrient broth. This nutrient broth was incubated for 16 hours at 30° C. at 150 rpm. Glucose was used as the sole carbon source. Autoclaved production media (modified Kannan and Rehacek media) was inoculated using the nutrient broth as the seed culture. Inoculated production media was then incubated for 48 hours at 30° C. at 200 rpm.
   Harvesting: The cells were harvested at 48 hours by centrifugation at 4600 rpm for 30 minutes. They were washed thrice, first with distilled water followed by 10% ethanol and then again with distilled water. The cells were homogenized using a homogenizer for approximately 15 minutes. The cells were then kept at −20° C. overnight after which they were placed in a freeze dryer for lyophilisation.
   Extraction: Polymer was extracted from the cells using the soxhlet extraction method. The cells were treated in a soxhlet apparatus with methanol for 24 hours, under reflux conditions, as a washing step to remove the impurities. After this, the methanol was replaced with chloroform which was used to extract the polymer from the cells. The cells were treated with chloroform for 4 hours under reflux conditions. This chloroform solution was concentrated using a rotary vacuum evaporator and the polymer was precipitated using ice-cold methanol solution. Extraction was continued using the same batch of cells by incubating them twice with chloroform for 24 hours under reflux conditions. This chloroform solution was again concentrated using the rotary vacuum evaporator and the polymer was precipitated using ice-cold methanol solution.
   Mechanical properties: Film samples were prepared by casting 10 ml of 10 w/v % polymer solution in chloroform into a glass petri dish (6 cm diameter). The samples were left covered at room temperature until solvent evaporation was complete (monitored by weight change). Mechanical properties were determined using tensile testing with samples cut from the solvent-cast film into strips of 5 mm width and 40 mm length. The thickness of the sample was around 300 µm. The crosshead speed was 10 mm/min.
   Elongation at break ($\varepsilon_U$) was determined as 2-4%. Young's modulus (E) of P(3HB) was determined as 1.3 GPa. Ultimate tensile strength ($\sigma_U$) reached 26 MPa.

Example 2—Production and Characterisation of poly(3-hydroxyoctanoate-co-3-hydroxydecanoate) "P(3HO-3HD)" from Glucose by *Pseudomonas mendocina* CH50

Producer organism: *Pseudomonas mendocina* CH50 obtained from the National Collection of Industrial and Marine Bacteria, NCIMB (deposit No. 10542).

Media composition:
Second stage (Mineral salt medium)
   Ammonium sulphate: 0.45 g/L
   Sodium hydrogen phosphate: 3.42 g/L
   Potassium dihydrogen phosphate: 2.38 g/L
Production media (Mineral salt medium)
   Ammonium sulphate: 0.50 g/L
   Sodium hydrogen phosphate: 3.80 g/L
   Potassium dihydrogen phosphate: 2.65 g/L
Carbon source
   glucose: 20 g/L
   Trace element solution: 1 ml/L
   Magnesium sulphate heptahydrate: 0.8 g/L
   Production: A single colony of *Pseudomonas mendocina* CH50 was used to inoculate the autoclaved nutrient broth. This nutrient broth was incubated for 16 hours at 30° C. at 150 rpm. Autoclaved second stage media was inoculated using the nutrient broth culture as the seed culture. Inoculated second stage media was then incubated at 30° C. at 150 rpm until the optical density reached 1.6 without dilution. This was used as the inoculum to inoculate the production media (10% culture volume). Inoculated production media was then incubated for 48 hours at 30° C. at 200 rpm.
   Harvesting: The cells were harvested at 48 hours by centrifugation at 4600 rpm for 30 minutes. They were washed thrice, first with distilled water followed by 10% ethanol and then again with distilled water. The cells were homogenized using a homogenizer for approximately 15 minutes. The cells were then kept at −20° C. overnight after which they were placed in a freeze dryer for lyophilisation.
   Extraction: Polymer was extracted from the cells using the soxhlet extraction method. The cells were incubated in the soxhlet with methanol for 24 hours under reflux conditions as a washing step to remove the impurities. After this, the methanol was replaced with chloroform which was used to extract the polymer from the cells. Extraction was continued using the same batch of cells by incubating them with chloroform for 24 hours under reflux conditions. This chloroform solution was concentrated using a rotary vacuum evaporator and the polymer was precipitated using ice-cold methanol solution. Yield: 43%, dry cell weight 0.57 g/l.
   Characterisation: The resulting polymer was characterised by GC-MS and NMR. The GC-MS results are presented in Table 1:

TABLE 1

|  | HO content (mol %) | HD content (mol %) |
| --- | --- | --- |
| Mean | 26.2 | 73.8 |
| SD | 1.0 | 1.7 |

$^1$H NMR and $^{13}$C NMR are presented in FIG. 1.

Thermal and morphological properties: The resulting P(3HO-3HD) polymer is a semi-crystalline polymer characterized by slow crystallization. Melting of the crystalline phase was observed only for aged samples. The crystalline phase was not detected by differential scanning calorimetry after melting of the polymer in a first heating cycle and cooling the sample at the rate of 20 K/min. The glass transition temperature determined by differential scanning calorimetry was in the range between −41° C. to −46° C. The crystalline phase of P(3HO-3HD) melted between 26 to 66° C. The highest melting rate (endothermic peak maximum) was 57±2° C. Enthalpy of fusion (crystallinity degree)

changed with polymer storage and for polymer aged at room temperature (for a period of 5 weeks) reached 27±2 J/g.

TABLE 2

| PHA | Tg (° C.) | Tm (° C.) | ΔH (J/g) |
|---|---|---|---|
| P(3HD-co-3HO) | −45.1 | 54.3 | 19.0 |

Mechanical properties: Film samples were prepared by casting 10 ml of 10 w/v % polymer solution in chloroform into a glass petri dish (6 cm diameter). The samples were left covered at room temperature until solvent evaporation was complete (monitored by weight change). Mechanical properties were determined by tensile testing using samples cut from the solvent-cast film into strips of 5 mm width and 40 mm length. The thickness of the sample was around 300 μm. The crosshead speed was 10 mm/min.

P(3HO-3HD) is a soft ductile polymer with elongation at break ($\varepsilon_U$) 580±30%. Young's modulus (E) of P(3HO-3HD) was determined as 8.7±1.1 MPa. Ultimate tensile strength ($\sigma_U$) reached 10.4±1.0 MPa.

Molecular weight (Mw) and polydispersity index (PDI) were determined by GPC. Mw was determined as 340 kDa and PDI as 2.7.

Example 3—Production and Characterisation of poly (3-hydroxyoctanoate-co-3-hydroxydecanoate-co-3-hydroxydodecanoate) "P(3HO-3HD-3HDD)" from coconut oil by *Pseudomonas mendocina* CH50

Producer organism: *Pseudomonas mendocina* CH50 obtained from NCIMB.
Media composition:
Second stage (Mineral salt medium)
    Ammonium sulphate: 0.45 g/L
    Sodium hydrogen phosphate: 3.42 g/L
    Potassium dihydrogen phosphate: 2.38 g/L
Production media (Mineral salt media)
    Ammonium sulphate: 0.50 g/L
    Sodium hydrogen phosphate: 3.80 g/L
    Potassium dihydrogen phosphate: 2.65 g/L
Carbon source
    Coconut oil: 20 g/L (obtained from Sigma Aldrich)
    Trace element solution: 1 ml/L
    Magnesium sulphate heptahydrate: 0.8 g/L
    Production: A single colony of *Pseudomonas mendocina* CH50 was used to inoculate the autoclaved nutrient broth. This nutrient broth was incubated for 16 hours at 30° C. at 150 rpm. Coconut oil was used as the sole carbon source. Autoclaved second stage media (MSM media) was inoculated using the nutrient broth culture as the seed culture. Inoculated second stage media was then incubated at 30° C. at 150 rpm until the optical density reached 1.6 without dilution. This was used as the inoculum to inoculate the production media (MSM media) (10% of the culture volume). The inoculated production media was then incubated for 48 hours at 30° C. at 200 rpm.
    Harvesting: The cells were harvested at 48 hours by centrifugation at 4600 rpm for 30 minutes. They were washed thrice, first with distilled water followed by 10% ethanol and then again with distilled water. The cells were homogenized using a homogenizer for approximately 15 minutes. The cells were then kept at −20° C. overnight after which they were placed in a freeze dryer for lyophilisation.

Extraction: Polymer was extracted from the cells using the soxhlet extraction method. The cells are incubated in the soxhlet with methanol for 24 hours at 90° C. under methanol refluxing conditions to remove the impurities. After this, the methanol solution was replaced with the chloroform which was used to extract the polymer from the cells. Extraction was continued using the same batch of cells by incubating them with chloroform for 24 hours under refluxing conditions. This chloroform solution was concentrated using the rotary vacuum evaporator and the polymer was precipitated using ice-cold methanol solution. Yield: 54% dry cell weight, 1.43 g/l.

Characterisation: The resulting polymer was characterised by GC-MS and NMR. The GC-MS results are presented in Table 3:

TABLE 3

| | HO content (mol %) | HD content (mol %) | HDD content (mol %) |
|---|---|---|---|
| Mean | 30.4 | 48.4 | 21.2 |
| SD | 2.1 | 0.8 | 2.0 |

$^1$H NMR and $^{13}$C NMR are presented in FIG. 2.

Thermal and morphological properties: P(3HO-3HD-3HDD) is a semi-crystalline polymer which is characterized by slow crystallisation. Melting of the crystalline phase was observed only for aged samples. The crystalline phase was not detected by differential scanning calorimetry after melting the polymer in a first heating cycle and cooling the sample at the rate of 20 K/min. The glass transition temperature determined by differential scanning calorimetry was in the range between −42° C. to −45° C. The crystalline phase of P(3HO-3HD-3HDD) melted between 25 to 56° C. The highest melting rate (endothermic peak maximum) was 48±2° C. Enthalpy of fusion (crystallinity degree) changed with polymer storage and for polymer aged at room temperature (for a period of 5 weeks) reached 16±1 J/g.

TABLE 4

| PHA | Tg (° C.) | Tm (° C.) | ΔH (J/g) |
|---|---|---|---|
| P(3HO-co-3HD-co-3HDD) | −42.8 | 48.6 | 11.4 |

Mechanical properties: Film samples were prepared by casting 10 ml of 10 w/v % polymer solution in chloroform into a glass petri dish (6 cm diameter). The samples were left covered at room temperature until solvent evaporation was complete (monitored by weight change). Mechanical properties were determined by tensile testing using samples cut from the solvent-cast film into strips of 5 mm width and 40 mm length. The thickness of the sample was around 300 μm. The crosshead speed was 10 mm/min.

P(3HO-3HD-3HDD) is a soft ductile polymer with elongation at break ($\varepsilon_U$) 580±50%. Young's modulus (E) of P(3HO-3HD-3HDD) was determined as 2.1±0.1 MPa. Ultimate tensile strength ($\sigma_U$) reached 6.0±1.0 MPa.

Molecular weight (Mw) and polydispersity index (PDI) were determined by GPC. Mw was determined as 333 kDa and PDI as 2.37.

Example 4—Production of Blends

All PHAs used in the procedure were purified by dissolving in chloroform followed by precipitation with methanol solution. This was repeated several times. The PLLA was a commercially available product (PL38 PURASORB) which was used without further purification.

Blends were produced by dissolving the blend components in a common solvent, chloroform, which is a good solvent for all PHAs and PLLA. Film samples were prepared by solvent casting of polymer solutions.

Polymer solutions were prepared by completely dissolving specified amounts of the first and second blend components in chloroform to achieve a final total polymer concentration of 5 w/v %. The blend solution was kept on the magnetic stirrer to allow mixing for 24 hours at room temperature. 10 ml of the resulting polymer solution was poured into a glass petri dish (6 cm diameter) and left covered at room temperature until solvent evaporation was complete (monitored by weight change).

Example 5—Testing of Blends

The blends prepared according to Example 4 were subjected to various tests to determine their mechanical properties. As a comparison, the same tests were carried out in respect of the known P(3HB)/P(3HO) blends (Lizarraga-Valderrama et al., Engineering in Life Sciences 15(6): 612-621, 2015).

Tensile Strength Testing: The following test method was used to determine tensile properties of the blend materials in the form of films (less than 1.0 mm in thickness).

Apparatus:
Device for Measurements of Specimen Geometry: LUJII 150-mm Electronic Digital Caliper or equivalent device accurate and precise to 0.01 mm.
Tensile Tester: Instron Model 5940 Single Column Tabletop Testing System with a 0.5 kN load cell or equivalent.
Gripping Devices: Instron 2710-102 Advanced Screw Side-Action Grips: capacity—500 N. Grip Faces: Rubber coated flat faces (Instron, Cat.: 2702-002)
Materials: Thin films (thinner than 1 mm) of PHA-based materials were prepared by solvent casting. After the films were dried to constant weights, they were packed into non-sealed polyethylene bags and stored at room temperature for 6 weeks.
Method: Preparation of Test Specimens: Cut strips with width of approximately 5 mm from a test film. A circular film disk prepared in a 60 mm Petri dish can be cut into 5 strips with the shortest strips around 36 mm. Cut at least 4 specimens. No specimen shall vary by more than 2% in width along its entire length. Utmost care must be exercised in cutting specimens to prevent nicks and tears along the edges of the specimen that are likely to cause premature failure.
Testing:
Measure and record the thickness of the test specimen to an accuracy of 0.01 mm, at least, in five different places within the gauge length area.
Set the initial gauge length (grip separation) at 23.0 mm and the rate of grip separation at 10.0 mm/min.
Place the specimen in the grips of the testing machine, taking care to align the long axis of the specimen with an imaginary line joining the points of attachment of the grips to the machine. The specimen should be aligned as perfectly as possible with the direction of pull so that no rotary motion that may induce slippage will occur in the grips. Tighten the grips evenly and firmly to the degree necessary to minimize slipping of the specimen during testing.

Start the test and record the load versus extension.

Repeat the testing for the series of specimens prepared.

Fixing a specimen of film sample in the grips of the testing machine always results in a degree of bending of the specimen. This results in an actual length of the sample larger than the set separation between the grips. Therefore the raw load (tensile stress) vs strain curves do not start from "0" separation distance. The initial specimen length is corrected by adding the separation distance, where load starts increasing, to the set distance between the grips. This correction factor is also used for correcting the current specimen deformation by deducing it from the measured separation.

Calculations:
Tensile Strength: Tensile stress ($\sigma$) is calculated by dividing the load (F) at a specific time point by the original cross-sectional area (A). The result is expressed in megaPascals (MPa) and reported to three significant figures:

$$\sigma = \frac{F}{A_0}$$

The ultimate tensile strength is defined as the maximal value of tensile stress in the stress-strain curve.

Elongation: Percent elongation ($\varepsilon$) is calculated by dividing the corrected distance ($l_i$) of grip separation by the corrected initial length of specimen ($l_0$) and multiplying by 100:

$$\varepsilon = \frac{l_i - l_0}{l_0} \times 100 = \frac{\Delta l}{l_0} \times 100$$

Young's Modulus: Young's modulus is calculated as a tangent to the initial linear portion of the stress-strain curve. Obtain the stress-strain curve, select a linear region usually between 0.5 to 1.5% of elongation of the specimen. Use data from this region to calculate a tangent using appropriate software. The result is expressed in gigapascals (GPa) and reported to three significant figures.

Results:

TABLE 5

Mechanical Characterisation of PHA polymer components

| Mechanical Properties | P(3HB) Example 1 | P(3HO-3HD) Example 2 | P(3HO-3HD-3HDD) Example 3 |
|---|---|---|---|
| $\sigma$, MPa | 26 | 10.4 | 6 |
| E, MPa | 1300 | 8.7 | 2.1 |
| $\varepsilon_b$, % | 2-4 | 580 | 580 |

TABLE 6

Mechanical Characterisation of known P(3HB)/P(3HO) BLENDS

| Mechanical Properties | P(3HB)/P(3HO) 25:75 | P(3HB)/P(3HO) 50:50 | P(3HB)/P(3HO) 75:25 |
|---|---|---|---|
| $\sigma$, MPa | 0.71 | 2.17 | 17.80 |
| E, MPa | 12 | 21 | 140 |
| $\varepsilon_b$, % | 73.8 | 94.1 | 41.30 |

TABLE 7

Mechanical Characterisation of P(3HB)/P(3HO-3HD) BLENDS

| Mechanical Properties | P(3HB)/P(3HO-3HD) 5:95 | P(3HB)/P(3HO-3HD) 10:90 | P(3HB)/P(3HO-3HD) 15:85 | P(3HB)/P(3HO-3HD) 20:80 | P(3HB)/P(3HO-3HD) 25:75 |
|---|---|---|---|---|---|
| σ, MPa | 10 | 5.7 | 4.1 | 3.2 | 1.9 |
| E, MPa | 12 | 19 | 19 | 22 | 28 |
| $\varepsilon_b$, % | 540 | 430 | 330 | 280 | 200 |

TABLE 8

Mechanical Characterisation of P(3HB)/P(3HO-3HD-3HDD) BLENDS

| Mechanical Properties | P(3HB)/P(3HO-3HD-3HDD) 5:95 |
|---|---|
| σ, MPa | 8.4 |
| E, MPa | 51 |
| $\varepsilon_b$, % | 510 |

TABLE 9

Mechanical Characterisation of PLLA/P(3HO-3HD) BLENDS

| Mechanical Properties | PLLA/P(3HO-3HD) 5:95 | PLLA/P(3HO-3HD) 10:90 | PLLA/P(3HO-3HD) 15:85 | PLLA/P(3HO-3HD) 20:80 | PLLA/P(3HO-3HD) 25:75 |
|---|---|---|---|---|---|
| σ, MPa | 14.3 | 4.9 | 3.6 | 6.5 | 7.2 |
| E, MPa | 84 | 21 | 240 | 470 | 500 |
| $\varepsilon_b$, % | 640 | 250 | 10.5 | 5.7 | 4.2 |

TABLE 10

Mechanical Characterisation of PLLA/P(3HO-3HD-3HDD) BLENDS

| Mechanical Properties | PLLA/P(3HO-3HD-3HDD) 5:95 |
|---|---|
| σ, MPa | 5.8 |
| E, MPa | 40 |
| $\varepsilon_b$, % | 350 |

Example 6—Dip Moulding Preparation of Tubes for Use as Nerve Conduits

P(3HB)/P(3HO-3HD) tubes with composition 15/85 were made from polymers by dip moulding using polymer solutions in chloroform.

Solutions of a polymer mixture of P(3HB)/P(3HO-3HD) were prepared by dissolving the required amounts of polymer in chloroform in order to obtain a total polymer concentration of 6 wt %. Clear solutions were used to form tubes on a cylindrical stainless steel mandrel with diameter 1.8 mm. Tubes were formed by multiple dipping of the mandrel into the polymer solutions. The tube formation was carried out at 25° C. Dipping and withdrawal rate was 200 mm/min. After complete mandrel withdrawal from the polymer solution, 30 sec drying time was used before conducting the next dip. After each series of 5 dippings, 4 min drying time was applied.

The total number of dips was 20 and produced polymeric tubes with a wall thickness of 150 μm. After the last dipping the tubes were left on a mandrel for complete solvent evaporation at room temperature for 5 days.

Example 7—Extrusion of Tubes for Use as Nerve Conduits

Porous P(3HB)/P(3HO-3HD) tubes with composition 15/85 were made by extrusion of a pre-mix of the polymers with 70 wt % of a powder of sodium chloride. Ground and sieved NaCl with a particle fraction smaller than 50 μm was used as porogen. For the preparation of the pre-mix the required amount of polymers were dissolved in chloroform in order to obtain polymer concentration of 8 wt %. The required amount of NaCl particles was added to the polymer solution under mechanical stirring. After dispersion of the NaCl particles in the polymer solution, the solution was poured into glass trays and the solvent was allowed to evaporate for 3 days at room temperature.

The pre-mix of polymer blend with NaCl was cut into small pieces using a kitchen blender. The pre-mix was used for tube extrusion at barrel temperature of 130° C. to produce tubes with a wall thickness around 200 μm. The extruded tubes were further processed to achieve porous tubes by leaching NaCl in water. The tubes were kept in a portion of water under gentle stirring for 7 days. The water was replaced on a daily basis. After washing out NaCl, the tubes were dried at room temperature resulting in porous tubes.

Example 8—Production and Characterisation of poly(3-hydroxybutyrate) "P(3HB)" from Walnut Oil by *Cupriavidus necator*

Producer Organism: *Cupriavidus necator* (Formerly Known as *Ralstonia eutropha*)

Production Media

Ammonium chloride: 4 g/L

Disodium hydrogen phosphate. 12 $H_2O$: 11 g/L

Potassium dihydrogen phosphate: 1.2 g/L (autoclaved at 121° C. for 15 minutes)

Carbon Source
  Walnut oil: 20 g/L (autoclaved at 121° C. for 15 minutes) (obtained from Waitrose Ltd.)
  Trace Element Solution: 1 ml/L (Filter Sterilized)
  Magnesium Sulphate Heptahydrate: 1.4 g/L (Autoclaved at 121° C. for 15 Minutes)
  Production: A single colony of Cupriavidus necator was used to inoculate the autoclaved nutrient broth. This nutrient broth was incubated for 24 hours at 30° C. at 150 rpm. Autoclaved production media was inoculated using the nutrient broth as the seed culture. Inoculated production media was then incubated for 48 hours at 30° C. at 200 rpm.
  Harvesting: The cells were harvested at 48 hours by centrifugation at 4600 rpm for 30 minutes. They were washed thrice, first with distilled water followed by 10% ethanol and then again with distilled water. The cells were homogenized using a homogenizer for approximately 15 minutes. The cells were then kept at −20° C. overnight after which they are placed in the freeze dryer for lyophilisation.
  Extraction: Polymer was extracted from the cells using soxhlet extraction method. The cells were incubated in the soxhlet with methanol for 24 hours under methanol refluxing conditions as a washing step to remove the impurities. After this, the methanol was replaced with chloroform which was used to extract the polymer from the cells. The cells are incubated with the chloroform for 4 hours under reflux conditions. This chloroform solution was concentrated using the rotary vacuum evaporator and the polymer was precipitated using ice-cold methanol solution. Extraction was continued using the same batch of cells by incubating them twice with chloroform solution at 70° C. for 24 hours. This chloroform solution was again concentrated using the rotary vacuum evaporator and the polymer was precipitated using ice-cold methanol solution. Yield: 50% dry cell weight, 1.97 g/l.
  Characterisation: The resulting polymer was characterised by GC-MS and NMR. $^1$H NMR and $^{13}$C NMR are presented in FIG. 3.
  Thermal and morphological properties: P(3HB) is a semi-crystalline polymer. Glass transition temperature determined by differential scanning calorimetry was in the range between 0° C. to 3° C. The crystalline phase of P(3HB) melted in the wide temperature range between 120 to 175° C. The highest melting rate (endothermic peak maximum) was 171±2° C. Enthalpy of fusion (crystallinity degree) changed with polymer storage and for polymer aged at room temperature reached 88±2 J/g.

TABLE 11

| PHA | Tg (° C.) | Tm (° C.) | ΔH (J/g) |
|---|---|---|---|
| P(3HB) | 2.9 | 168.4 | 71.4 |

Mechanical properties: Film samples were prepared by casting 10 ml of 10 w/v % polymer solution in chloroform into a glass petri dish (6 cm diameter). The samples were left covered at room temperature until solvent evaporation was complete (monitored by weight change). Mechanical properties were determined by tensile testing using samples cut from the solvent-cast film into the strips of 5-mm width and 40-mm long. The thickness of the sample was around 200 μm. The crosshead speed was 5 mm/min.

P(3HB) is a rigid polymer with elongation at break ($\varepsilon_U$) 2-4%. Young's modulus (E) of P(3HB) was 1.3±0.2 GPa. Ultimate tensile strength ($\sigma_U$) reached 26±2 MPa.

Molecular weight (Mw) and polydispersity index (PDI) were determined by GPC. Mw was determined as 606 kDa and PDI as 2.5.

The P(3HB) polymer may be used as the second component in a blend according to the invention.

Example 9—Production and Characterisation of poly (3-hydroxyoctanoate-co-3-hydroxydecanoate) "P(3HO-3HD)"—23 mol % HO, 77 mol % HD Producer Organism: Pseudomonas mendocina CH50
Media Composition:
Second Stage (Mineral Salt Medium)
  Ammonium sulphate: 0.45 g/L
  Sodium hydrogen phosphate: 3.42 g/L
  Potassium dihydrogen phosphate: 2.38 g/L (autoclaved at 121° C. for 15 minutes)
Production Media (Mineral Salt Media)
  Ammonium sulphate: 0.50 g/L
  Sodium hydrogen phosphate: 3.80 g/L
  Potassium dihydrogen phosphate: 2.65 g/L (autoclaved at 121° C. for 15 minutes)
Carbon Source
  Sugarcane molasses: 20 g/L (bought from Holland and Barret) (autoclaved at 110° C. for 10 minutes)
Trace Element Solution: 1 ml/L (Filter Sterilized)
Magnesium sulphate heptahydrate: 0.8 g/L (autoclaved at 121° C. for 15 minutes)
  Production: A single colony of Pseudomonas mendocina CH50 was used to inoculate the autoclaved nutrient broth. This nutrient broth was incubated for 16 hours at 30° C. at 150 rpm. Autoclaved second stage media was inoculated using the nutrient broth culture as the seed culture. Inoculated second stage media was then incubated at 30° C. at 150 rpm until the optical density reached 1.6 without dilution. This was used as the inoculum to inoculate the production media (10% culture volume). Inoculated production media was then incubated for 48 hours at 30° C. at 200 rpm.
  Harvesting: The cells were harvested at 48 hours by centrifugation at 4600 rpm for 30 minutes. They were washed thrice, first with distilled water followed by 10% ethanol and then again with distilled water. The cells were homogenized using a homogenizer for approximately 15 minutes. The cells were then kept at −20° C. overnight after which they are placed in the freeze dryer for lyophilisation.
  Extraction: Polymer was extracted from the cells using soxhlet extraction method. The cells were incubated in the soxhlet with methanol for 24 hours under reflux conditions as a washing step to remove the impurities. After this, the methanol was replaced with chloroform which was used to extract the polymer from the cells. Extraction was carried out by incubating the cells with chloroform solution for 24 hours under reflux conditions. This chloroform solution was concentrated using the rotary vacuum evaporator and the polymer was precipitated using ice-cold methanol solution. Yield: 37.5% dry cell weight, 0.46 g/l.
  Characterisation: The resulting polymer was characterised by GC-MS and NMR. $^1$H NMR and $^{13}$C NMR are presented in FIG. 4.
  Thermal and morphological properties: P(3HO-3HD) is a semi-crystalline polymer which is characterized by slow crystallization. Melting of the crystalline phase was observed only for aged samples. The crystalline phase was not detected by differential scanning calorimetry after melting the polymer in first heating cycle and cooling the sample at the rate of 20 K/min. Glass transition temperature determined by differential scanning calorimetry was in the range between −41° C. to −46° C. The crystalline phase of P(3HO-3HD) melted between 28 to 70° C. The highest melting rate (endothermic peak maximum) was 53±2° C.

Enthalpy of fusion (crystallinity degree) changed with polymer storage and for polymer aged at room temperature reached 21±2 J/g.

TABLE 12

| PHA | Tg (° C.) | Tm (° C.) | ΔH (J/g) |
|---|---|---|---|
| P(3HO-co-3HD) | −41.5 | 53.0 | 21.0 |

Mechanical properties: Film samples were prepared by casting 10 ml of 10 w/v % polymer solution in chloroform into a glass petri dish (6 cm diameter). The samples were left covered at room temperature until solvent evaporation was complete (monitored by weight change). Mechanical properties were determined by tensile testing using samples cut from the solvent-cast film into the strips of 5-mm width and 40-mm long. The thickness of the sample was around 300 μm. The crosshead speed was 10 mm/min.

P(3HO-3HD) is a soft ductile polymer with elongation at break ($\varepsilon_U$) 635±25%. Young's modulus (E) of P(3HO-3HD) was 11.4±0.3 MPa. Ultimate tensile strength ($\sigma_U$) reached 15.1±0.3 MPa.

Molecular weight (Mw) and polydispersity index (PDI) were determined by GPC. Mw was determined as 449.3 kDa and PDI as 1.5.

The P(3HO-3HD) polymer may be used as the first component in a blend according to the invention.

The invention claimed is:

1. A nerve guidance conduit having a body which comprises a polymer blend comprising:
   (a) from 60 to 98 wt. % of a first component which is a PHA copolymer comprising two or more different medium chain length hydroxyalkanoate monomer units; and
   (b) from 2 to 40 wt. % of a second component which is either a PHA homopolymer containing a short chain length hydroxyalkanoate monomer unit, or a polylactide (PLA).

2. A nerve guidance conduit as claimed in claim 1, wherein the first component is a binary or ternary PHA copolymer.

3. A nerve guidance conduit as claimed in claim 1, wherein the PHA copolymer comprises hydroxyalkanoate monomer units which, independently of one another, contain 6 or more carbon atoms.

4. A nerve guidance conduit as claimed in claim 3, wherein the PHA copolymer comprises hydroxyalkanoate monomer units which, independently of one another, contain 8, 10 or 12 carbon atoms.

5. A nerve guidance conduit as claimed in claim 1, wherein the PHA copolymer comprises hydroxyalkanoate units which are independently selected from 3-hydroxy and 4-hydroxyalkanoates.

6. A nerve guidance conduit as claimed in claim 5, wherein each hydroxyalkanoate unit is a medium chain length 3-hydroxyalkanoate.

7. A nerve guidance conduit as claimed in claim 6, wherein each hydroxyalkanoate unit is independently selected from the group consisting of 3-hydroxyoctanoate (3HO), 3-hydroxydecanoate (3HD) and 3-hydroxydodecanoate (3HDD).

8. A nerve guidance conduit as claimed in claim 1, wherein the PHA copolymer is poly(3-hydroxyoctanoate-co-3-hydroxydecanoate) or poly(3-hydroxyoctanoate-co-3-hydroxydecanoate-co-3-hydroxydodecanoate).

9. A nerve guidance conduit as claimed in claim 1, wherein the chirality of the hydroxy-substituted carbon atom in each hydroxyalkanoate unit in the PHA copolymer is of the R-configuration.

10. A nerve guidance conduit as claimed in claim 1, wherein the first component is a binary PHA copolymer which contains 3-hydroxydecanoate (3-HD) monomer units in an amount ranging from 60 mol % to 85 mol % (based on the weight average molecular weight, Mw, of the PHA copolymer) and/or 3-hydroxyoctanoate monomer units in an amount from 20 to 35 mol % (based on the weight average molecular weight, Mw, of the PHA copolymer).

11. A nerve guidance conduit as claimed in claim 1, wherein the first component is a ternary PHA copolymer which contains 3-hydroxydecanoate (3-HD) monomer units in an amount ranging from 40 mol % to 60 mol % (based on the weight average molecular weight, Mw, of the PHA copolymer) and/or 3-hydroxyoctanoate monomer units in an amount from 20 to 40 mol % (based on the weight average molecular weight, Mw, of the PHA copolymer).

12. A nerve guidance conduit as claimed in claim 1, wherein the first component is a PHA copolymer which contains 3-hydroxydodecanoate (3-HDD) monomer units in an amount ranging from 10 to 30 mol % (based on the weight average molecular weight, Mw, of the PHA copolymer).

13. A nerve guidance conduit as claimed in claim 1, wherein the PHA copolymer has a molecular weight in a range from 50 to 600 kDa.

14. A nerve guidance conduit as claimed in claim 1, wherein the PHA copolymer is obtained or obtainable by culturing of a microorganism selected from *Pseudomonas putida, Pseudomonas oleovorans, Pseudomonas mendocina* CH50, *Pseudomonas fluorescence, Pseudomonas aeruginosa, Pseudomonas raguenesii, Pseudomonas guezennei, Pseudomonas stutzeri, Pseudomonas cepacia*, and *Comamonas testosteronii*.

15. A nerve guidance conduit as claimed in claim 14, wherein said microorganism is *Pseudomonas mendocina* CH50.

16. A nerve guidance conduit as claimed in claim 14, wherein said microorganism is grown in a culture medium which comprises glucose or coconut oil as a carbon source.

17. A nerve guidance conduit as claimed in claim 1, wherein the second component of the polymer blend is a PHA homopolymer containing a short chain length hydroxyalkanoate monomer unit.

18. A nerve guidance conduit as claimed in claim 17, wherein the PHA homopolymer comprises hydroxyalkanoate monomer units which each contain 3, 4 or 5 carbon atoms.

19. A nerve guidance conduit as claimed in claim 18, wherein the PHA homopolymer is poly(3-hydroxybutyrate).

20. A nerve guidance conduit as claimed in claim 1, wherein the PHA homopolymer has a molecular weight in a range from 200 kDa to 2 MDa.

21. A nerve guidance conduit as claimed in claim 1, wherein the PHA homopolymer is obtained or obtainable by culturing of a microorganism selected from *Cupriavidus necator, Alcaligenes latus, Bacillus cereus, Aeromonas caviae, Rhodospirillum rubrum, Methylobacterium extorquens, Halomonas boliviensis* LC1, *Bacillus subtilis*, and *Bacillus megaterium*.

22. A nerve guidance conduit as claimed in claim 21, wherein said microorganism is *Bacillus subtilis* OK2.

23. A nerve guidance conduit as claimed in claim 21, wherein said microorganism is grown in the presence of a culture medium which comprises glucose as a carbon source.

24. A nerve guidance conduit as claimed in claim 1, wherein the second component of the polymer blend is a polylactide (PLA).

25. A nerve guidance conduit as claimed in claim 24, wherein the second component of the polymer blend is poly(L-lactic acid).

26. A nerve guidance conduit as claimed in claim 1, wherein the polymer blend is selected from one of the following:
P(3HO-3HD)/P(3HB)
P(3HO-3HD-3HDD)/P(3HB)
P(3HO-3HD-3HDD)/PLA
P(3HO-3HD)/PLA
P(3HO-3HD-3HDD)/PLLA
P(3HO-3HD)/PLLA
P(3HO-3HD-3HDD)/PDLA
P(3HO-3HD)/PDLA.

27. A nerve guidance conduit as claimed in claim 1, wherein the first component is present in an amount in a range from 80 to 85 wt. % (based on the total weight of the blend).

28. A nerve guidance conduit as claimed in claim 1, wherein the second component is a PHA homopolymer which is present in an amount in a range from 15 to 25 wt. % (based on the total weight of the blend).

29. A nerve guidance conduit as claimed in claim 1, wherein the second component is a polylactide which is present in an amount in a range from 3 to 10 wt. % (based on the total weight of the blend).

* * * * *